(12) United States Patent
Edwards, Jr. et al.

(10) Patent No.: US 12,324,830 B2
(45) Date of Patent: Jun. 10, 2025

(54) **METHODS OF TREATMENT FOR *CANDIDA AURIS* INFECTIONS**

(71) Applicant: LOS ANGELES BIOMEDICAL RESEARCH INSTITUTE AT HARBOR-UCLA MEDICAL CENTER, Torrance, CA (US)

(72) Inventors: John E. Edwards, Jr., Palos Verdes Estates, CA (US); Shakti Singh, Carson, CA (US); Ashraf S. Ibrahim, Irvine, CA (US); Priya Uppuluri, Torrance, CA (US)

( * ) Notice: Subject to any disclaimer, the term of this patent is extended or adjusted under 35 U.S.C. 154(b) by 908 days.

(21) Appl. No.: 17/046,169

(22) PCT Filed: Apr. 10, 2018

(86) PCT No.: PCT/US2018/026889
§ 371 (c)(1),
(2) Date: Oct. 8, 2020

(87) PCT Pub. No.: WO2019/199279
PCT Pub. Date: Oct. 17, 2019

(65) Prior Publication Data
US 2021/0030852 A1 Feb. 4, 2021

(51) Int. Cl.
*A61K 39/00* (2006.01)
*A61K 39/395* (2006.01)
*A61K 45/06* (2006.01)
*A61P 31/10* (2006.01)
*C07K 16/14* (2006.01)

(52) U.S. Cl.
CPC .... *A61K 39/0002* (2013.01); *A61K 39/39575* (2013.01); *A61K 45/06* (2013.01); *A61P 31/10* (2018.01); *C07K 16/14* (2013.01); *A61K 2039/545* (2013.01); *A61K 2039/55* (2013.01)

(58) Field of Classification Search
CPC .......... A61K 39/0002; A61K 39/39575; A61K 45/06; A61K 2039/545; A61K 2039/55; A61K 31/4164; A61K 31/4196; A61K 31/496; A61K 31/506; A61K 31/7048; A61K 38/12; A61K 38/16; A61K 2039/505; A61K 2039/55505; A61K 2300/00; A61P 31/10; C07K 16/14; C07K 14/40; G01N 2333/40; G01N 2800/52
See application file for complete search history.

(56) References Cited

U.S. PATENT DOCUMENTS

| | | |
|---|---|---|
| 10,130,691 B2 | 11/2018 | Ibrahim et al. |
| 10,653,757 B2 | 5/2020 | Yeaman et al. |
| 2007/0077256 A1 | 4/2007 | Edwards, Jr. et al. |
| 2008/0311135 A1 | 12/2008 | Zheng et al. |

FOREIGN PATENT DOCUMENTS

| | | | |
|---|---|---|---|
| CN | 103998056 A | 8/2014 | |
| CN | 105407915 A | 3/2016 | |
| JP | 2012-255031 A | 12/2012 | |
| WO | 2006/059228 A2 | 6/2006 | |
| WO | 2007/081896 A2 | 7/2007 | |
| WO | 2007/126813 A2 | 11/2007 | |
| WO | WO-2016142660 A1 * | 9/2016 | ....... A61K 39/39575 |
| WO | WO-2017155949 A1 * | 9/2017 | ............. A61K 31/00 |

OTHER PUBLICATIONS

Liu, Y and Filler, SG "Candida albicans Als3, a Multifunctional Adhesin and Invasin", 2011, Eukaryotic Cell, 10(2), 168-173. (Year: 2011).*
Larkin, E et al. "The Emerging Pathogen Candida auris: Growth Phenotype, Virulence Factors, Activity of Antifungals, and Effect of SCY-078, a Novel Glucan Synthesis Inhibitor, on Growth Morphology and Biofilm Formation", 2017, Antimicrob. Agents and Chemother., 61(5), 1-13. (Year: 2017).*
Sears, D and Schwartz, BS "Candida auris: An emerging multidrug-resistant pathogen", 2017, International Journal of Infectious Diseases, 63, 95-98. (Year: 2017).*
Bar, E et. al. "A Novel Th Cell Epitope of Candida albicans Mediates Protection from Fungal Infection", 2012, The Journal of Immunology, 188(11), 5636-5643. (Year: 2012).*
Sharma, C et. al. "Whole genome sequencing of emerging multidrug resistant Candida auris isolates in India demonstrates low genetic variation", 2016, New Microbes and New Infections, 13, 77-82. (Year: 2016).*
Patent Cooperation Treaty, International Search Report issued in PCT/US2018/026889, Jul. 11, 2018, pp. 1-4.
Patent Cooperation Treaty, Written Opinion issued in PCT/US2018/026889, Jul. 11, 2018, pp. 1-13.
Patent Cooperation Treaty, International Preliminary Report on Patentability issued in PCT/US2018/026889, Oct. 13, 2020, pp. 1-14.
Kaur et al., "Strategies to Reduce Mortality in Adult and Neonatal Candidemia in Developing Countries", Journal of Fungi, Jul. 19, 2017, pp. 1-20, vol. 3, No. 3: 41.
Chowdhary et al., "Candida auris: A rapidly emerging cause of hospital-acquired multidrug-resistant fungal Infections globally", PLoS Pathogens, May 18, 2017, pp. 1-10, vol. 13, No. 5: e1006290.
Sherry et al., "Biofilm-Forming Capability of Highly Virulent, Multidrug-Resistant Candida auris", Emerging Infectious Diseases, Feb. 28, 2017, pp. 328-331, vol. 23(2).
Sui et al., "The vaccines and antibodies associated with Als3p for treatment of Candida albicans infections", Vaccine, 2017, pp. 5786-5793, vol. 35.

(Continued)

*Primary Examiner* — Nelson B Moseley, II
*Assistant Examiner* — Alyssa Rae Stonebraker
(74) *Attorney, Agent, or Firm* — Pillsbury Winthrop Shaw Pittman LLP

(57) ABSTRACT

Disclosed herein are compositions and methods for treating and immunizing against *C. auris* infection and colonization. The compositions and methods include polypeptides and fragments derived from the *C. albicans* Als3 protein, homologs thereof, and antibodies or fragments thereof that specifically bind these polypeptides and fragments. Administration of these compositions confers treatment and resistance against *C. auris* infection and colonization.

14 Claims, 12 Drawing Sheets

Specification includes a Sequence Listing.

(56) References Cited

OTHER PUBLICATIONS

Spellberg et al., "Efficacy of the Anti-Candida rAls3p-N or rAls1p-N Vaccines against Disseminated and Mucosal Candidiasis", Journal of Infectious Diseases, Jul. 15, 2006, pp. 256-260, vol. 194(2).

Tsay et al., "Approach to the Investigation and Management of Patients With Candida auris, an Emerging Multidrug-Resistant Yeast", Clinical Infectious Diseases, Aug. 17, 2017, pp. 306-311, vol. 66(2).

Larkin et al., The Emerging Pathogen Candida auris: Growth Phenotype, Virulence Factors, Activity of Antifungals, and Effect of SCY-078, a Novel Glucan Synthesis Inhibitor, on Growth Morphology and Biofilm Formation , Antimicrobial Agents and Chemotherapy, May 1, 2017, pp. 1-13, vol. 61(5).

The National Intellectual Property Administration of P. R. C., Official Action issued in Chinese Patent Application No. 201880094034. 8, Jan. 31, 2024, pp. 1-11.

\* cited by examiner

Score Expect Method Identities Positives Gaps Frame

(1) 153 bits(387) 3e-41() Compositional matrix adjust. 110/419(26%) 197/419(47%) 54/419(12%)

81 % (9/11)

```
TGVFNSFNSLT
TGVF S +SLT
TGVFTSIDSLT
```

70 % (17/24)

```
GDTFTLNMPCVFKFTT SQTSVDLT
GDTF L +P V +F T ++S+ ++
GDTFFLRIPFVIEFNT DESSIQMS
```

76 % (10/13)

```
GTVTLPLAFNVGGT
GT+T P+ FN G +
GTITFPIVFNAGFS
```

82 % (19/23)

```
TCSSNGIFITYKNVPAGYRPFVD
+CS+ G+ + + N+PAG+RP+++
SCSAAGVNVAFSNLPAGFRPYIN
```

75 % (15/20)

```
TKTIEILKPIPTTTITTSYV-GVTTSYS
T+ + I PIPT+TIT+++ VT++Y+
TRIVSIDTPIPTSTITSTWTESVTSTYT
```

77 % (17/22)

```
VTTSYSTKTAPIGETATVIVDI
VT++Y+ +P G TA+VIV++
VTSTYTVPASP-GVTASVIVEV
```

Score Expect Method Identities Positives Gaps Frame

(2) 28.9 bits(63) 1.7() Compositional matrix adjust. 13/42(31%) 20/42(47%) 0/42(0%)

75 % (15/20)

```
PTWNAVLGWSLDGTSASPGDTFTLNMPCVFKFTTSQTSVDLT
P + +GW +DG PGDT +N + + + T LT
PRFAKDIGWDIDGEGYKPGDTIIVNKNTKYYYDRTLTGEKLT
```

FIG. 1

Secondary Antibody Only
Control Mouse Serum
Anti-NDV-3A Mouse Serum

250 CFU/200 ul/Well 48 Hours

| Conc: µg/ml=> | 64.00 | 32.00 | 16.00 | 8.00 | 4.00 | 2.00 | 1.00 | 0.500 | 0.250 | 0.125 | 0.063 | 0.031 |
|---|---|---|---|---|---|---|---|---|---|---|---|---|
| Fluconazole | 0.355 | 0.336 | 1.221 | 1.394 | 1.271 | 1.285 | 1.294 | 1.310 | 1.354 | 1.306 | 0.960 | 0.356 |

| Conc: µg/ml=> | 16.00 | 8.00 | 4.00 | 2.00 | 1.00 | 0.500 | 0.250 | 0.125 | 0.063 | 0.031 | 0.016 | 0.008 |
|---|---|---|---|---|---|---|---|---|---|---|---|---|
| Amphitericin B | 0.076 | 0.071 | 0.083 | 0.164 | 0.506 | 0.785 | 0.814 | 0.933 | 0.867 | 0.625 | 0.786 | 0.597 |
| Posaconazole | 0.066 | 0.066 | 0.065 | 0.100 | 0.073 | 0.072 | 0.076 | 0.068 | 0.060 | 0.060 | 0.072 | 0.056 |
| Micafungin | 0.162 | 0.374 | 0.367 | 0.369 | 0.396 | 0.907 | 1.015 | 1.019 | 0.770 | 0.536 | 0.502 | 0.455 |
| Caspofungin | 0.347 | 0.189 | 0.173 | 1.017 | 0.515 | 0.530 | 0.537 | 0.560 | 0.591 | 0.587 | 0.703 | 0.939 |
| Isavuconazole | 0.059 | 0.060 | 0.065 | 0.099 | 0.107 | 0.109 | 0.096 | 0.108 | 0.145 | 0.116 | 0.157 | 0.154 |
| Amplyx APX001 | 0.057 | 0.056 | 0.053 | 0.068 | 0.056 | 0.057 | 0.058 | 0.057 | 0.075 | 0.097 | 0.164 | 0.110 |
| DMSO | 1.018 | 0.750 | 0.643 | 0.900 | 0.901 | 0.944 | 0.946 | 0.957 | 0.966 | 1.097 | 1.043 | 0.955 |
| No Drug | 1.246 | 1.307 | 1.340 | 1.389 | 1.376 | 1.313 | 1.366 | 1.347 | 1.353 | 1.345 | 1.402 | 1.196 |

FIG. 8B

METHODS OF TREATMENT FOR *CANDIDA AURIS* INFECTIONS

BACKGROUND OF THE INVENTION

*Candida auris* is a pathogenic yeast species that poses a newly emerging global health threat. The yeast can enter the bloodstream and spread throughout the body, causing serious invasive infections. Additionally, *C. auris* is known to cause severe wound, ear, respiratory, and urinary infections. *C. auris* infections can be difficult to treat because they are often resistant to commonly used antifungal drugs. Accordingly, new methods of treatment for and prevention of *C. auris* infections are needed.

SUMMARY OF THE INVENTION

Disclosed herein are compositions and methods for treating and immunizing against *C. auris* infection. Featured are polypeptides, antibodies, and methods of use thereof for providing active and passive immunoprotection against *C. auris* infection.

In one aspect, featured is a method of treating a subject (e.g., a human subject) for, or immunizing a subject (e.g., a human subject) against, a *C. auris* infection by administering to the subject an immunogenic amount of an Als3 polypeptide or fragment or homolog thereof or an anti-Als3 antibody or antigen-binding fragment thereof. Also featured is a method of preventing *C. auris* infection in a subject by administering to the subject an immunogenic amount of an Als3 polypeptide or fragment or homolog thereof or an anti-Als3 antibody or antigen-binding fragment thereof. Also featured is a method of inducing an immune response to *C. auris* or production of antibodies to *C. auris* in a subject by administering to the subject an immunogenic amount of an Als3 polypeptide or fragment or homolog thereof. The methods may further include identifying the subject as having a *C. auris* infection prior to administration. The methods may further include identifying the subject as being colonized with *C. auris* prior to administration. The methods may further include identifying the subject as at risk of becoming colonized and/or infected with *C. auris* prior to administration. The subject may have, is suspected of having, or is at risk of having a *C. auris* infection. The subject may have been exposed to, or is suspected of being exposed to *C. auris*. The identifying step may include obtaining a sample from the subject. The sample may be obtained with a swab of the skin or mucous membranes (e.g., subject's mouth, throat, esophagus, rectum, or vagina).

In some embodiments, the method of administration inhibits or reduces *C. auris* burden or biofilm formation (e.g., by about 10%, 20%, 30%, 40%, 50%, 60%, 70%, 80%, 85%, 90%, or substantially eliminates) in the subject, relative to *C. auris* burden or biofilm formation in an untreated subject.

The subject may be immunocompromised, suffer from a comorbidity, and/or have a risk factor for *C. auris* infection. The comorbidity may be a bacterial infection, a fungal infection, a viral infection, an immune disorder, or diabetes. The fungal infection may be candidiasis (e.g., of a mucous membrane such as the mouth, throat, or esophagus), vulvovaginal candidiasis (e.g., recurrent vulvovaginal candidiasis), and/or invasive candidiasis. Exemplary risk factors are surgery, a stay in an intensive care unit, habitation in a nursing home, use of a breathing tube or a feeding tube, treatment with a broad-spectrum antibiotic or antifungal agent, or presence of a catheter (e.g., a central venous catheter).

The subject may be one that is being treated at, has been treated at, or will be treated at a hospital or health center. The subject may also be one that works at, has worked at, or will work at a hospital or health center.

The subject may be at least 50, 60, 70, 80, or 90 years old. Alternatively, the subject may be a newborn, infant, or toddler (e.g., less than 3 years old).

In some embodiments, the *C. auris* may be multi-drug resistant.

The methods described herein may reduce *C. auris* colonization (e.g., by about 10%, 20%, 30%, 40%, 50%, 60%, 70%, 80%, 85%, 90%, or substantially eliminate colonization). The methods may increase survival of the subject (e.g., by about 10%, 20%, 30%, 40%, 50%, 60%, 70%, 80%, 85%, 90%, 100%, or more), relative to an untreated subject with *C. auris* infection or colonization. The methods may reduce the number of days of active *C. auris* infection in the subject (e.g., by 1, 2, 3, 4, 5, 6, 7, 8, 9, 10, 20, 30, 40, 50, or more days), reduce the number of days of hospitalization of the subject (e.g., by 1, 2, 3, 4, 5, 6, 7, 8, 9, 10, 20, 30, 40, 50, or more days), reduce the number of days requiring antifungal therapy of the subject (e.g., by 1, 2, 3, 4, 5, 6, 7, 8, 9, 10, 20, 30, 40, 50, or more days), and/or reduce the dose and/or frequency of antifungal therapy needed by the subject, each relative to an untreated subject.

In some embodiments, the Als3 polypeptide or fragment or homolog thereof or anti-Als3 antibody or antigen-binding fragment thereof is administered subcutaneously, intramuscularly, intradermally, transdermally, intranasally, orally, or via an infusion. Preferably, the Als3 polypeptide or fragment is administered by intradermal or intramuscular injection. Preferably, the anti-Als3 antibody or antigen-binding fragment thereof is administered by infusion (e.g., intravenous infusion).

The Als3 polypeptide or fragment or homolog thereof or anti-Als3 antibody or antigen-binding fragment thereof may be administered with an additional therapeutic agent, such as an antifungal drug. The antifungal drug may be an azole (e.g., triazole (e.g., fluconazole, albaconazole, efinaconazole, epoxiconazole, isavuconazole, itraconazole, posaconazole, propiconazole, ravuconazole, terconazole, or voriconazole), an imidazole (e.g., bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, or tioconazole), or a thiazole (e.g., abafungin)), a polyene (e.g., amphotericin B, candicidin, filipin, hamycin, natamycin, nystatin, or rimocidin), an allylamine (e.g., amorolfin, butenafine, naftifine, or terbinafine), an echinocandin (e.g., anidulafungin, biafungin, caspofungin, or micafungin), a lanosterol demethylase inhibitor (e.g., VT-1161), benzoic acid, ciclopirox oamine, enfumafungin, 5-flucytosin, griseofulvin, haloprogin, tolnaftate, aminocandin, chlordantoin, chlorphenesin, nifuroxime, undecylenic acid, or crystal violet.

The additional therapeutic agent and the Als3 polypeptide or fragment or homolog thereof or anti-Als3 antibody or antigen-binding fragment thereof and the additional therapeutic agent can be administered within 1 month, 2 weeks, 1 week, 1 day, 12 hours, 6 hours, or 1 hour of each other, or at substantially the same time (e.g., serially in any order). The Als3 polypeptide or fragment thereof may be administered as an admixture with the additional therapeutic agent (e.g., antifungal drug).

The Als3 polypeptide or fragment or homolog thereof may have at least 85% (e.g., 90%, 95%, 97%, 99%, or 100%) identity to any one of SEQ ID NOs: 1-7. The anti-Als3 antibody or antigen-binding fragment thereof may be an antibody or antigen-binding fragment thereof that specifically binds to an epitope within a polypeptide having the amino acid sequence set forth in any one of SEQ ID NOs: 1-7 (e.g., with a $K_D$ of 100 nM or less, such as a $K_D$ of between about 1 pM and 100 nM, inclusive of the endpoints).

A dose of about 5 micrograms to about 5 milligrams (e.g., 10 to about 600 micrograms, about 20 to about 300 micrograms, about 30 to about 90 micrograms, 30 to 300, or about 200 to about 300 micrograms) of the Als3 polypeptide or fragment or homolog thereof may be administered to the subject in a single dose or diluted into one or more separate doses. The dose may be administered in a volume of about 2 mL or less (e.g., about 1 mL or less, about 0.75 mL or less, about 0.5 mL or less, or about 0.25 mL or less). Preferably, the Als3 polypeptide or fragment thereof is administered at a dose of 300 micrograms/0.5 mL.

The Als3 polypeptide or fragment or homolog thereof may be formulated with an adjuvant (e.g., Freund's adjuvant, lipopolysaccharide, aluminum phosphate, aluminum hydroxide, or alum). Preferably, the adjuvant is alum. The adjuvant may be present at a concentration about 0.1-10 mg/mL (e.g., 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1 mg/mL, 2 mg/mL, 3 mg/mL, 4 mg/mL, 5 mg/mL, 6 mg/mL, 7 mg/mL, 8 mg/mL, 9 mg/mL, or 10 mg/mL) and about 5%-90% (e.g., 10%, 15%, 20%, 25%, 30%, 35%, 40%, 45%, 50%, 55%, 60%, 65%, 70%, 75%, 80%, 85%, 90%) of the solution. Preferably, about 600 micrograms Als3 polypeptide is formulated with about 0.5 mg aluminum hydroxide in phosphate-buffered saline.

The Als3 polypeptide or fragment or homolog thereof may be administered to the subject more than once (e.g., 2, 3, 4, 5, 6, 7, 8, 9, 10, or more times, e.g., at the same or at a different dose). The second dose may be administered between about 7 and 90 days (e.g., between about 21 and 60 days) after administration of the first dose.

In some embodiments, the anti-Als3 antibody or antigen-binding fragment thereof can be administered at a dose of about 0.5 grams to about 5 grams. For example, the anti-Als3 antibody or antigen-binding fragment thereof may be administered at a dose of about 1 mg/kg to about 20 mg/kg and/or in a volume of about 1000 mL or less (e.g., 900 mL, 800 mL, 700 mL, 600 mL, 500 mL, 400 mL, 300 mL, 200 mL, 100 mL, 50 mL, or 10 mL or less, or a volume between about 1000 mL and 10 mL). In particular, the anti-Als3 antibody or antigen-binding fragment thereof may be administered at a concentration of about 0.5 mg/mL (e.g., 2 mg/mL) to about 500 mg/mL (e.g., up to 200 mg/mL). The anti-Als3 antibody or antigen-binding fragment thereof may be administered as an infusion, such as a continuous infusion or a bolus infusion. The anti-Als3 antibody or antigen-binding fragment thereof may be prepared as a lyophilized composition that is hydrated prior to administration. The anti-Als3 antibody or antigen-binding fragment thereof may be administered to the subject more than once (e.g., 2, 3, 4, 5, 6, 7, 8, 9, 10, or more times, e.g., at the same or at a different dose). The second dose may be administered to the subject within 1, 2, 3, 4, 5, 6, 7, 8, 9, 10, 11, or 12 months or more after the first dose, or in the event the *C. auris* infection has not resolved after administration of the first (or a subsequent) dose.

Definitions

As used herein, "adjuvant" refers to one or more substances that cause and/or enhance stimulation of the immune system. In this context, an adjuvant is used to enhance an immune response to one or more vaccine antigens (e.g., one or more of the Als3 polypeptides described herein). An adjuvant may be administered to a subject before, in combination with, or after administration of a vaccine. Examples of chemical compounds used as adjuvants include, but are not limited to, aluminum compounds (e.g., alum, aluminum hydroxide, aluminum phosphate, ALHYDROGEL®, ADJU-PHOS®), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

As used herein, a "conservative substitution" in an amino acid sequence refers to substitution of an amino acid with an amino acid having similar charge, polarity, and/or size. Preferably, a conservative substitution does not alter the structure or function of the protein or polypeptide.

As used herein, "fusion protein" refers to a protein that includes a polypeptide of the invention (e.g., an Als3 polypeptide, including fragments, homologs, and variants thereof) and a fusion partner (e.g., a heterologous polypeptide).

As used herein, "Als3 polypeptide" refers to any polypeptide, fragment, or variant, thereof sharing substantial sequence identity with *C. albicans* Als3. This includes, for example, the polypeptides of SEQ ID NOs: 1-5 and fragments thereof. Variants of an Als3 polypeptide have at least 50% (e.g., 55%, 60%, 65%, 70%, 75%, 80%, 85%, 90%, 95%, 97%, 98%, 99%, or 100%) sequence identity to the sequence of, e.g., any one of SEQ ID NOs: 1-5.

As used herein, "Als3 homolog" refers to a polypeptide derived from a common ancestral gene as Als3. Homologs include orthologs, which are genes in different species that evolved from a common ancestral gene. Als3 orthologs include, e.g., *C. auris* hypothetical proteins QG37_06265 (Genbank Accession No. XP 018167572.1) and QG37_05979 (Genbank Accession No. XP_018167307.1). A homolog or ortholog may share at least 10% sequence identity and/or sequence similarity to an Als3 polypeptide (e.g., 10%, 20%, 30%, 40%, 50%, 60%, 70%, 80%, 85%, 90%, 95%, 97%, 98%, 99%, or 100% sequence identity and/or sequence similarity to an Als3 polypeptide; such as at least 50% or greater sequence identity to an Als3 polypeptide having the sequence of any one of SEQ ID NOs: 1-5).

As used herein, "immunogenic" refers any substance that is capable of inducing an immune response in a subject (e.g., as determined by an increase in antibody titer in the subject, such as determined by ELISA, antibody subclass determination, an opsonophagocytosis assay (see, e.g., Dwyer and Gadjeva, *Methods Mol. Biol.* 1100:373-379, 2014), or the presence of cellular anamnesis, e.g., CD4+ and/or CD8+ cellular responses, e.g., using flow cytometry or MHC tetramer staining).

As used herein, "immunogenic amount" in the context of an immunogenic composition or vaccine refers to an amount of the composition that induces an immune response in a subject (e.g., as determined by an increase in antibody titer in the subject, such as determined by ELISA, antibody subclass determination, an opsonophagocytosis assay (see, e.g., Dwyer and Gadjeva, *Methods Mol. Biol.* 1100:373-379, 2014), or the presence of cellular anamnesis, e.g., CD4+ and/or CD8+ cellular responses, e.g., using flow cytometry or MHC tetramer staining).

As used herein, "immunogenic composition" refers to a composition that elicits an immune response in a subject to which it is administered (e.g., as determined by an increase in antibody titer in the subject, such as determined by ELISA, antibody subclass determination, an opsonophagocytosis assay (see, e.g., Dwyer and Gadjeva, *Methods Mol. Biol.* 1100:373-379, 2014), or the presence of cellular anamnesis, e.g., CD4+ and/or CD8+ cellular responses, e.g., using flow cytometry or MHC tetramer staining).

By "isolated" or "purified" is meant separated from other naturally accompanying components. Typically, a compound (e.g., nucleic acid, polypeptide, antibody, or small molecule) is substantially isolated when it is at least 60% (e.g., 70%, 80%, 85%, 90%, 95%, 97%, 99%, or 100%) by weight, free from the proteins and/or naturally occurring organic molecules with which it is naturally associated.

As used herein, a "patient" or "subject" refers to a mammal, including, but not limited to, a human or non-human mammal, such as a bovine, equine, canine, ovine, or feline.

The terms "polypeptide," and "protein" as used interchangeably herein, refer to any chain of two or more natural or unnatural amino acids, regardless of post-translational modification (e.g., glycosylation or phosphorylation), constituting all or part of a naturally-occurring or non-naturally occurring polypeptide or peptide, as is described herein.

As used herein, "pharmaceutical composition" refers to a composition containing a polypeptide or antibody as described herein, formulated with a pharmaceutically acceptable excipient or carrier. Pharmaceutically acceptable excipients or carriers are auxiliary substances that do not induce an immune response in the individual receiving the composition and do not deleteriously affect the properties of the composition.

As used herein, "specifically binds" refers to a binding reaction which is determinative of the presence of an antigen (e.g., an Als3 polypeptide) in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 µM and 100 nM). An antibody or antigen-binding fragment thereof that does not exhibit specific binding to a particular antigen or epitope thereof will exhibit a $K_D$ of greater than 100 nM (e.g., greater than 500 nm, 1 µM, 100 µM, 500 µM, or 1 mM) for that particular antigen or epitope thereof. A variety of immunoassay formats may be used to select antibodies specifically immunoreactive with a particular protein (e.g., an Als3 polypeptide), such as solid-phase ELISA immunoassays.

As used herein, "substantially identical" refers to an amino acid sequence or nucleic acid sequence that exhibits at least 50% sequence identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference amino acid or nucleic acid sequence, respectively. In general, for polypeptides, the length of comparison sequences can be at least five amino acids, e.g., 10, 20, 30, 40, 50, 60, 70, 80, 90, 100, 125, 150, 175, 200, 250, 300, 400, 500, 600, 700, 800, 900, 1000, 1100, or more amino acids, up to the entire length of the polypeptide (see, e.g., SEQ ID NOs: 1, 2, 3, 4, 5, 6, and 7). Preferably the comparison is up to the entire length of the polypeptide.

As used herein, when a polypeptide or nucleic acid sequence is referred to as having "at least X % sequence identity" to a reference sequence, it is meant that at least X percent of the amino acids or nucleotides in the polypeptide or nucleic acid, respectively, are identical to those of the reference sequence when the sequences are optimally aligned. An optimal alignment of sequences can be determined in various ways that are within the skill in the art, for instance, using the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

As used herein, the terms "treatment" or "treating" refer to reducing, decreasing, decreasing the progression of, or decreasing the side effects of (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) a *C. auris* infection. To determine whether the treatment is effective, a comparison can be made between the treated subject and a similarly-situated subject (e.g., one with, or at risk of, a *C. auris* infection) who did not receive the treatment. A comparison can also be made between the treated subject and a control, a baseline, or a known level or measurement. Treating a *C. auris* infection includes one or more of reducing *C. auris* colonization, infection burden, and biofilm formation (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%), as well as reducing the number of days of active *C. auris* infection in the subject (e.g., by 1, 2, 3, 4, 5, 6, 7, 8, 9, 10, 20, 30, 40, 50, or more days), reducing the number of days of hospitalization of the subject (e.g., by 1, 2, 3, 4, 5, 6, 7, 8, 9, 10, 20, 30, 40, 50, or more days), reducing the number of days requiring antifungal therapy of the subject (e.g., by 1, 2, 3, 4, 5, 6, 7, 8, 9, 10, 20, 30, 40, 50, or more days), and/or reducing the dose of antifungal therapy needed by the subject.

As used herein, the term "preventing" means decreasing the risk of (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) contracting a *C. auris* infection. To determine whether the prevention is effective, a comparison can be made between the subject who received the composition (e.g., Als3 polypeptide or fragment or homolog thereof or anti-Als3 antibody or antigen-binding fragment thereof) and a similarly-situated subject (e.g., one at risk of a *C. auris* infection) who did not receive the composition. A comparison can also be made between the subject who received the composition and a control, a baseline, or a known level or measurement.

BRIEF DESCRIPTION OF THE DRAWINGS

FIG. 1 is a schematic diagram showing regions of sequence identity between the Als3 protein (SEQ ID NO: 1)

and two Als3 orthologs in *C. auris*: hypothetical proteins QG37_06265 (Genbank Accession No. XP_018167572.1; SEQ ID NO: 6) and QG37_05979 (Genbank Accession No. XP_018167307.1; SEQ ID NO: 7).

Figure 2:
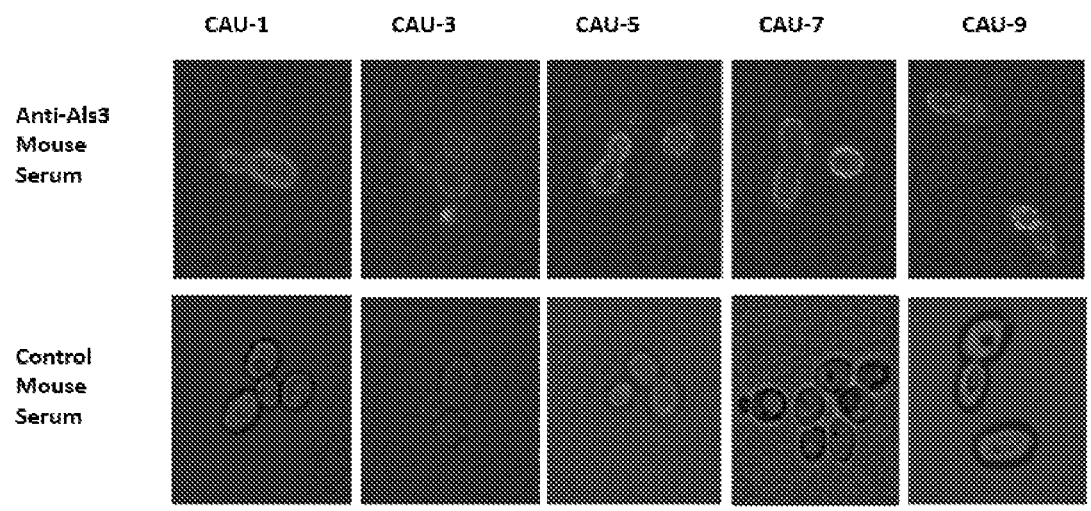

FIG. 2 is a series of confocal microscopy images showing anti-Als3 IgG antibodies binding to five different *C. auris* strains (CAU-1, CAU-3, CAU-5, CAU-7, CAU-9) obtained from the Center for Disease Control (CDC). Serum from mice inoculated with Als3-2 (SEQ ID NO: 2) bound the surface of *C. auris* (top row), while serum from a control mouse that was not inoculated with Als3-2 did not (bottom row).

Figure 3A:
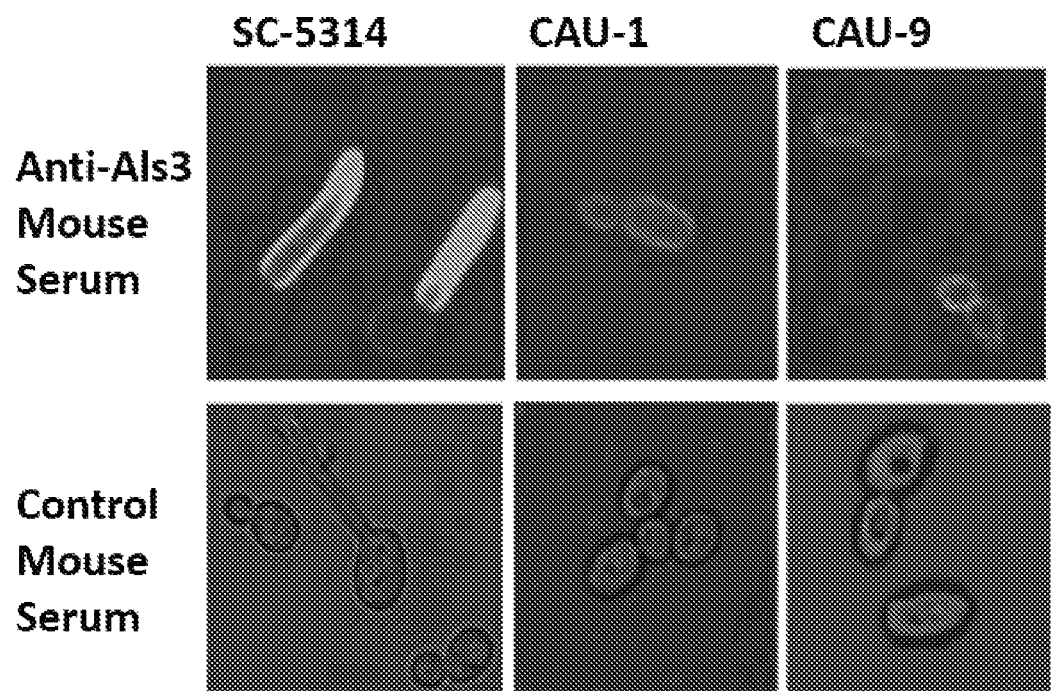

FIG. 3A is a series of confocal microscopy images showing anti-Als3 IgG antibodies binding to *C. albicans* strain SC-5314. The confocal microscopy images of anti-Als3 IgG antibodies binding to *C. auris* strains CAU-1 and CAU-9 from FIG. 2 are shown for comparison.

Figure 3B:
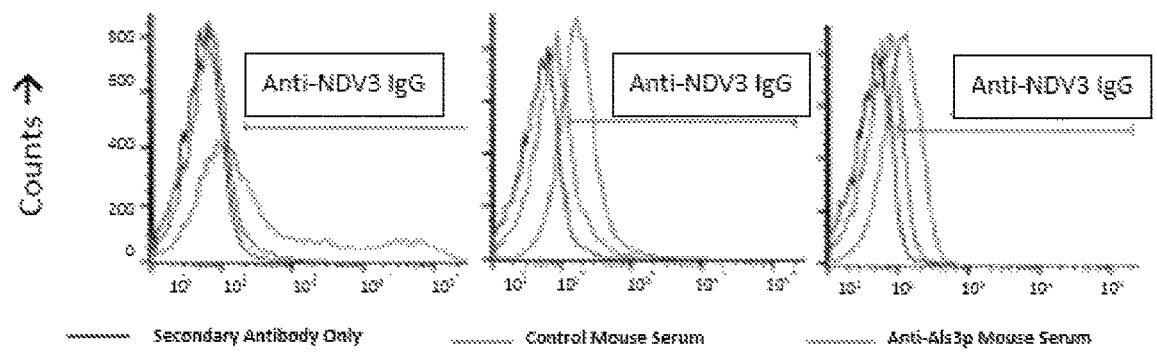

FIG. 3B is a set of graphs showing binding of anti-Als3 IgG antibodies to the *C. auris* cell surface, as determined by flow cytometry.

Figure 4:
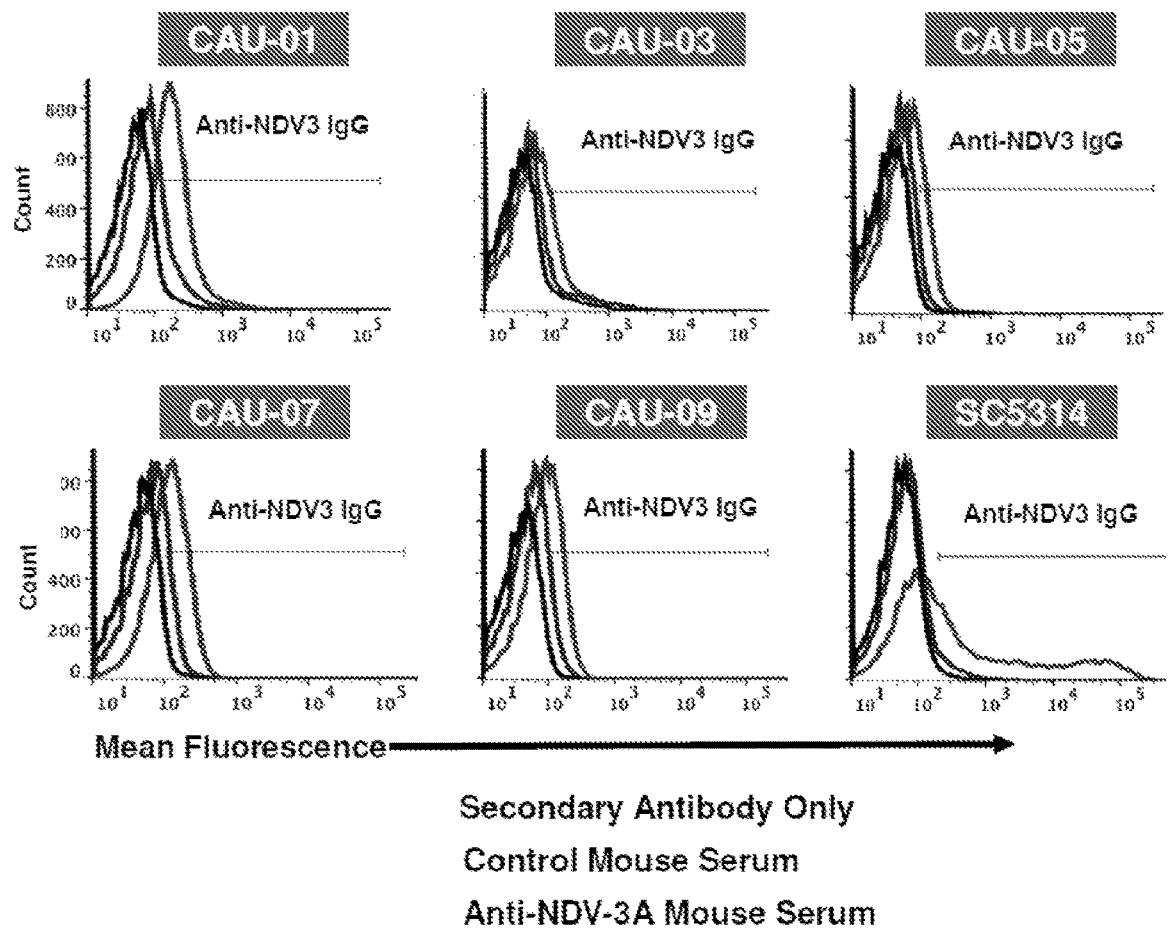

FIG. 4 is a graph showing binding of anti-Als3 IgG antibodies to different clinical strains of *C. auris*.

Figure 5:
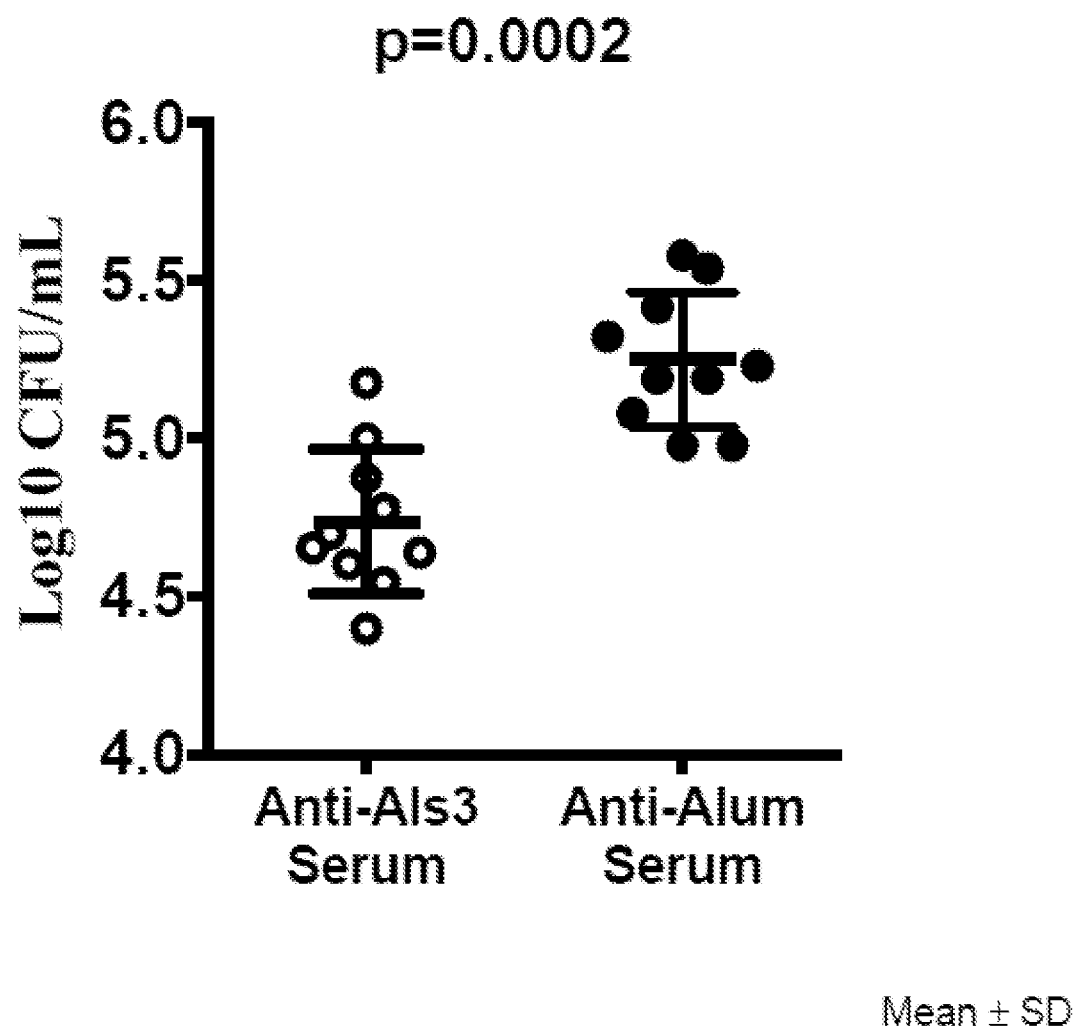

FIG. 5 is a graph showing that serum from NDV-3A vaccinated mice enhances opsonophagocytic killing of *C. auris*.

Figure 6:
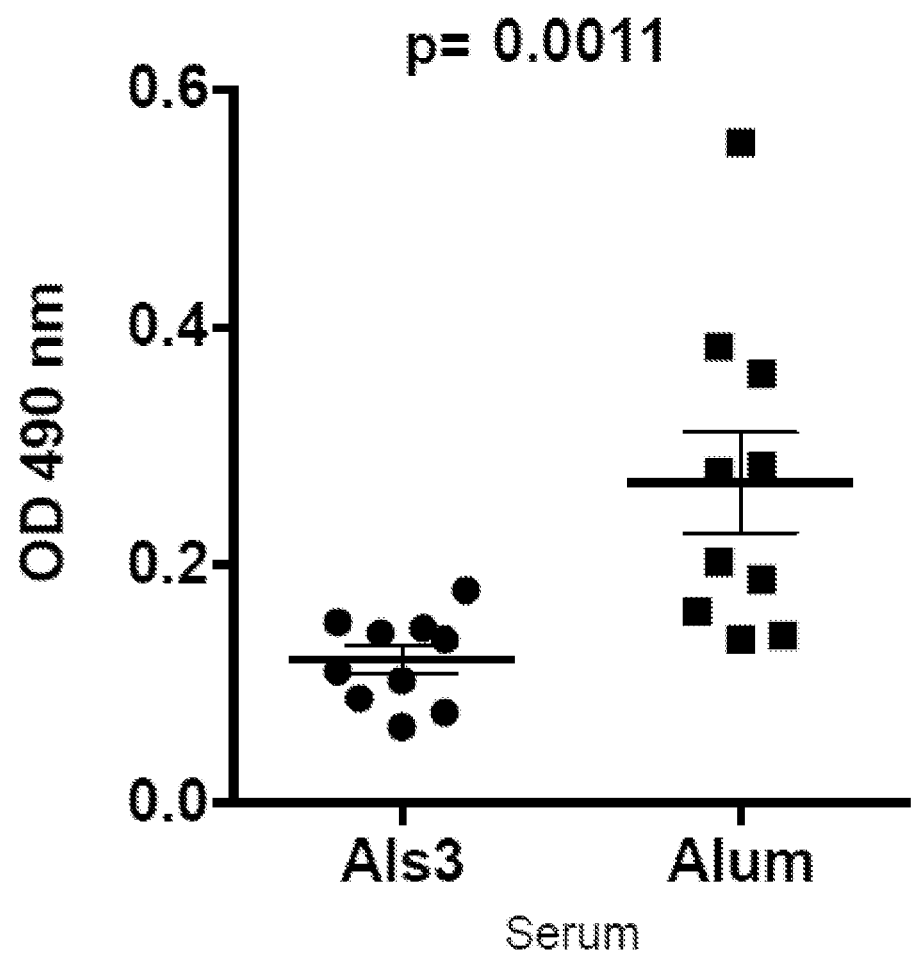

FIG. 6 is a graph showing that serum from NDV-3A vaccinated mice inhibits *C. auris* biofilm formation.

Figure 7:
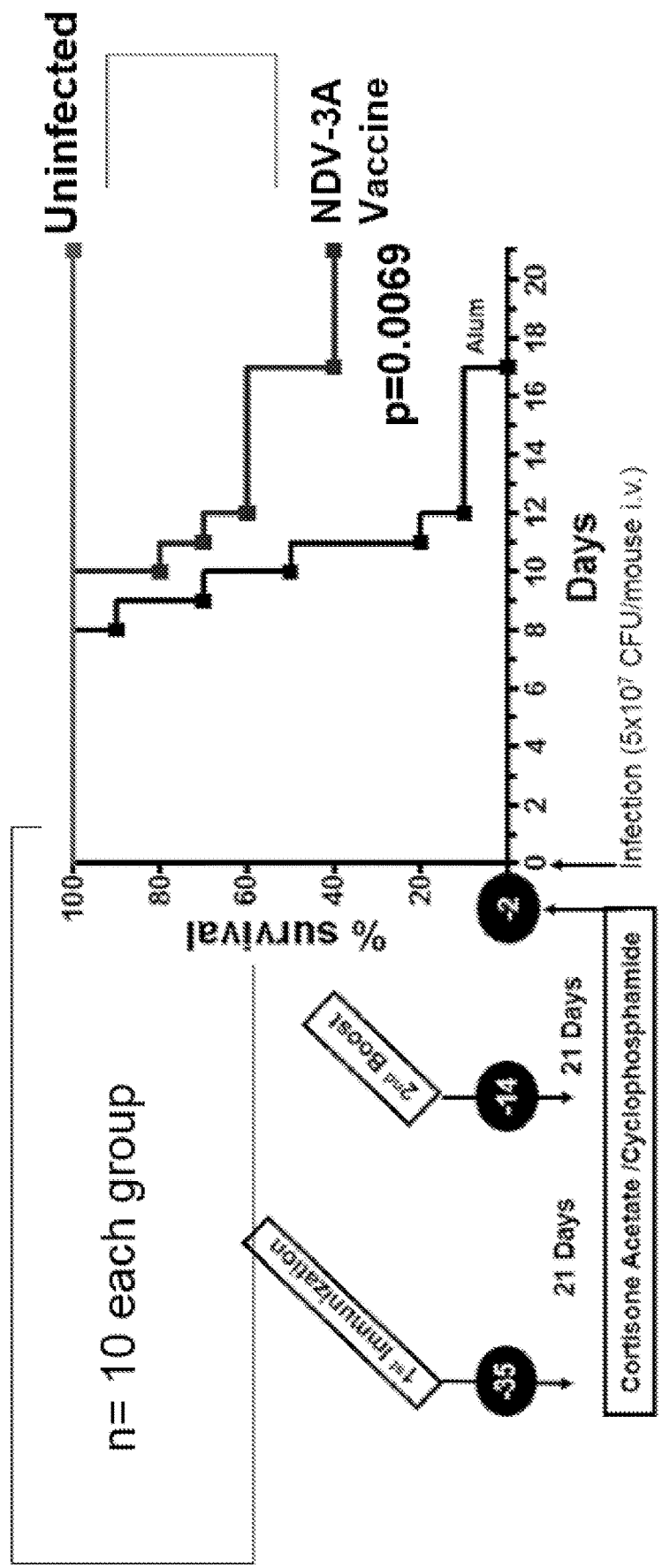

FIG. 7 is a schematic diagram and graph showing the schedule of vaccine administration and survival of vaccinated mice after infection with *C. auris*. 300 µg Als3-2 protein formulated with 200 µg Alum was subcutaneously administered to each mouse. 200 µg Alum was used as a control.

Figure 8A:
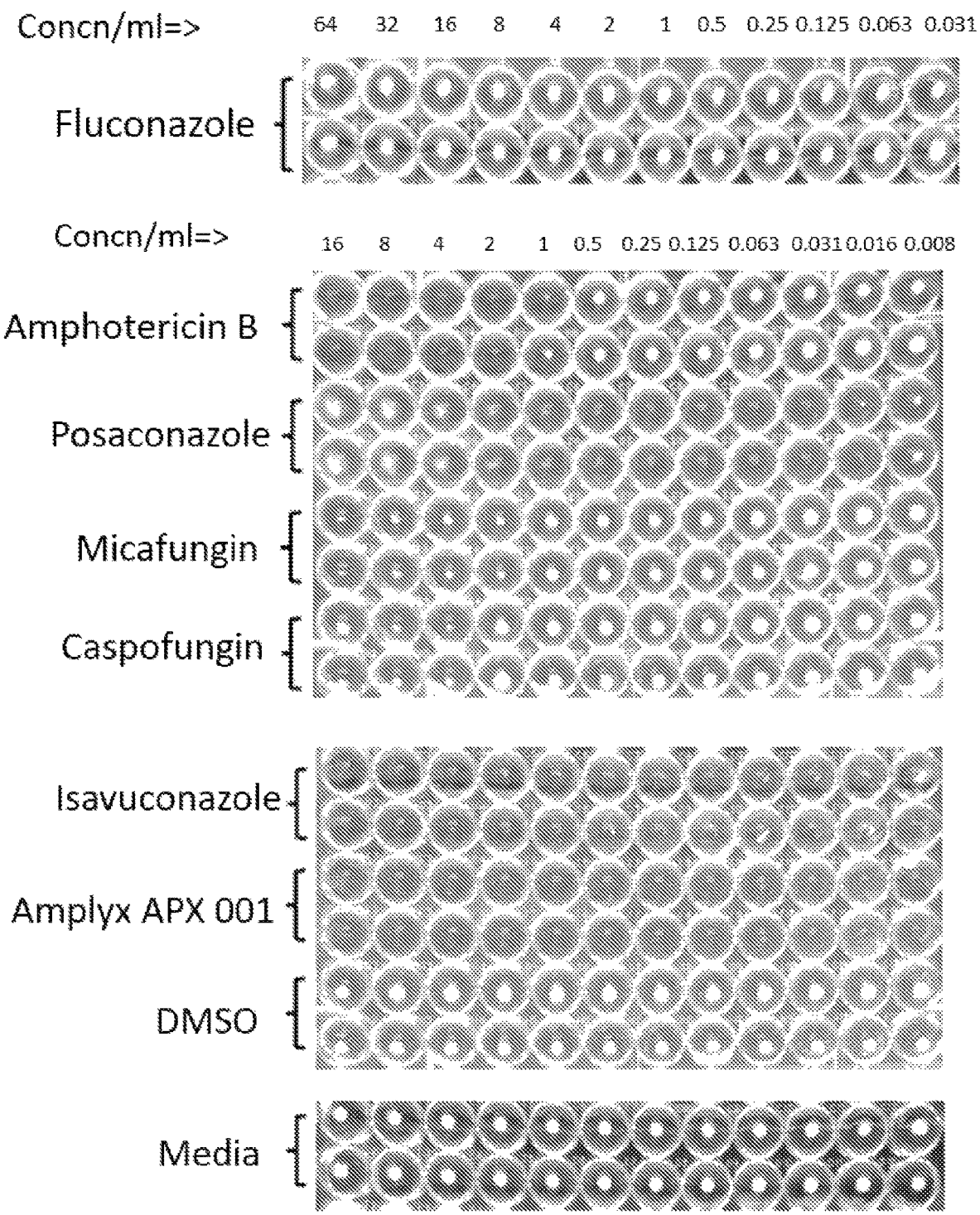

FIG. 8A is a set of images showing *C. auris* (strain CAU-09) colony growth after treatment with various types and concentrations of antifungal drugs.

FIG. 8B is a quantification of the minimum inhibitory concentrations (MIC) of antifungal agents obtained from the images shown in FIG. 8A.

Figure 9:
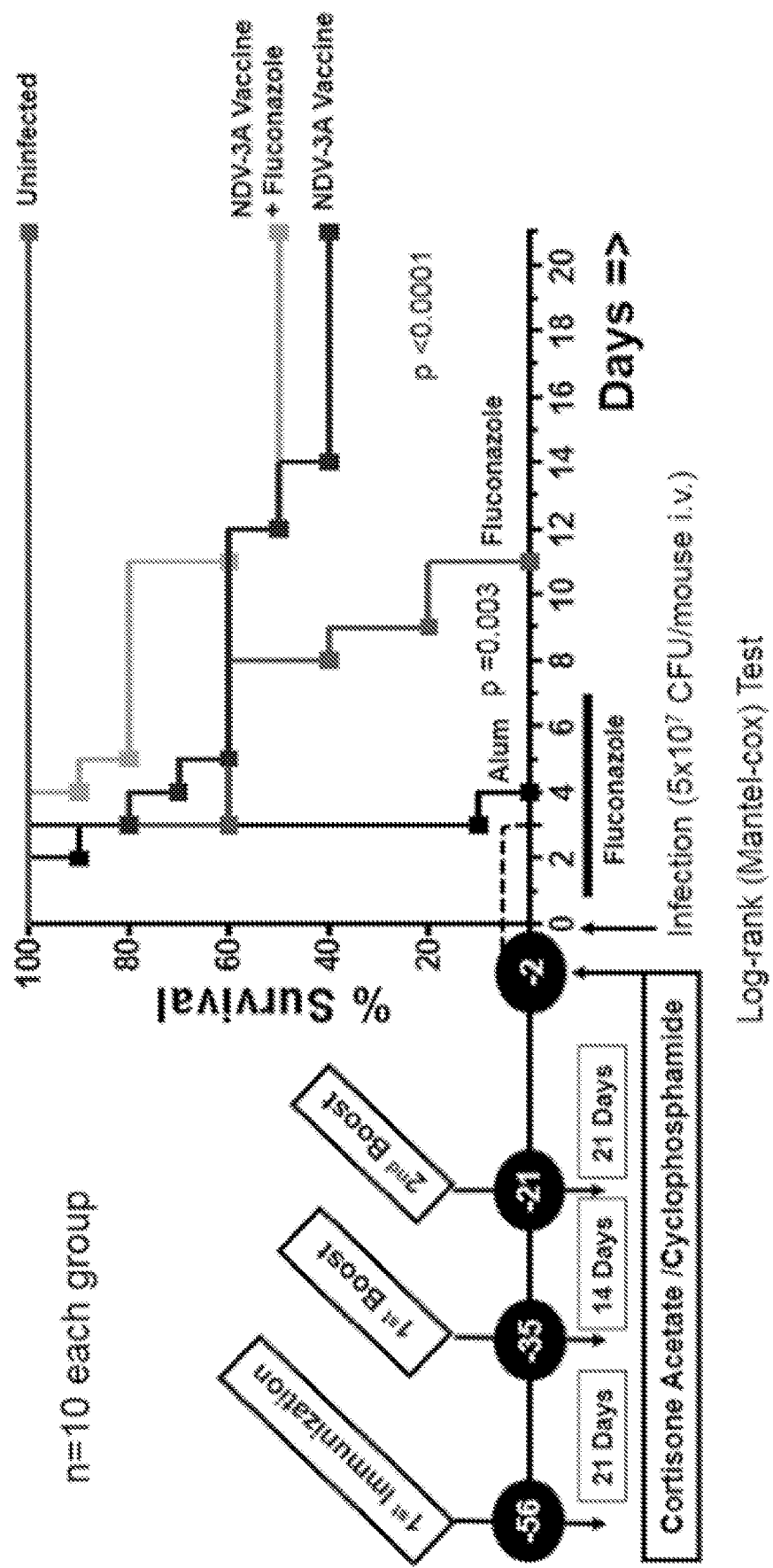

FIG. 9 is a graph showing survival of *C. auris* infected mice that have been vaccinated with NDV-3A and/or treated with the antifungal drug fluconazole (5 mg/kg body weight). 300 µg Als3-2 protein formulated with 200 µg Alum was subcutaneously administered to each mouse indicated as "NDV-3A vaccine." 200 µg Alum alone (Alum) was used as a control.

Figure 10:
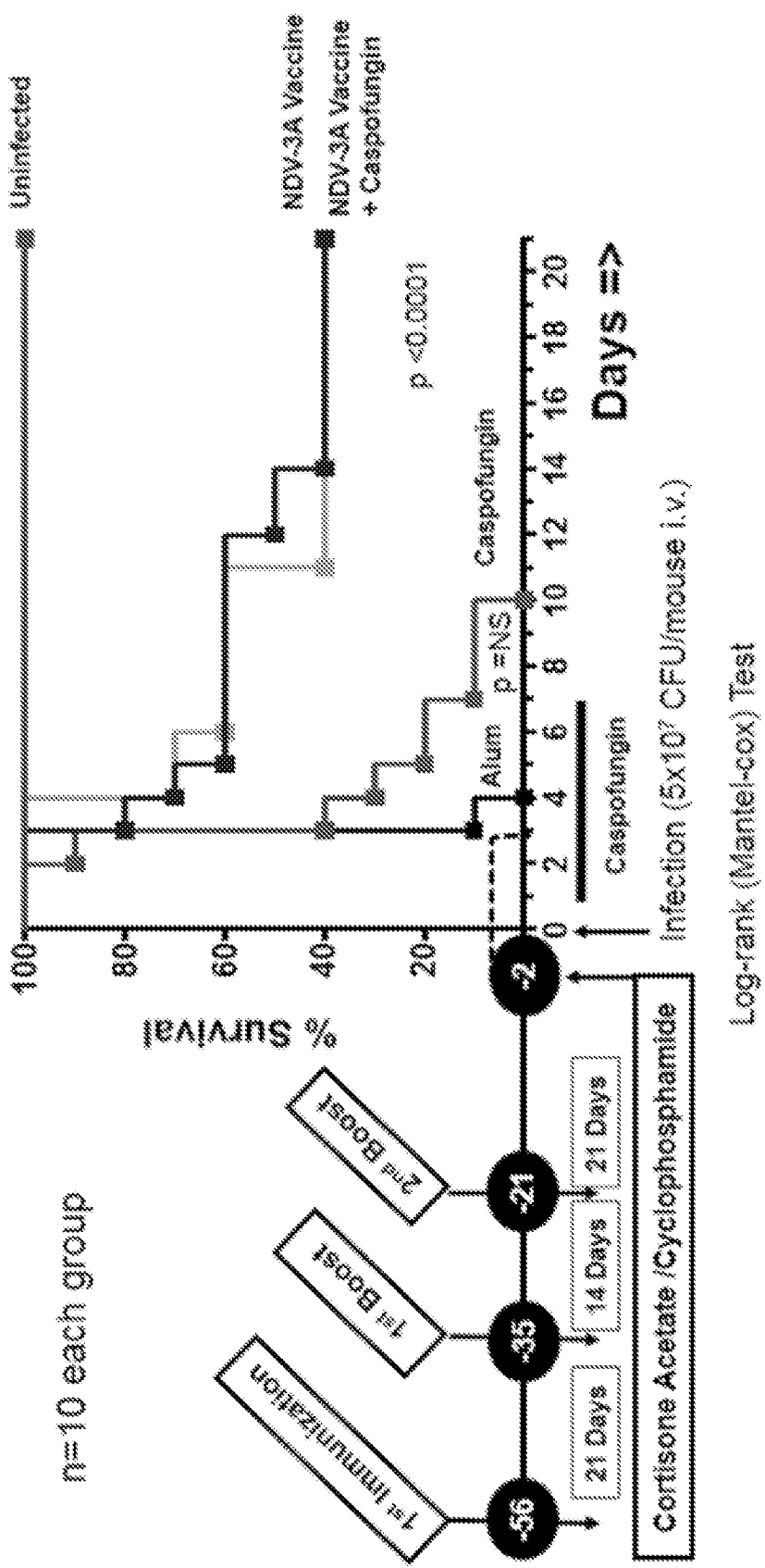

FIG. 10 is a graph showing survival of *C. auris* infected mice that have been vaccinated with NDV-3A and treated with the antifungal drug caspofungin (0.1 mg/kg body weight). 300 µg Als3-2 protein formulated with 200 µg Alum was subcutaneously administered to each mouse indicated as "NDV-3A vaccine." 200 µg Alum alone (Alum) was used as a control.

Figure 11:
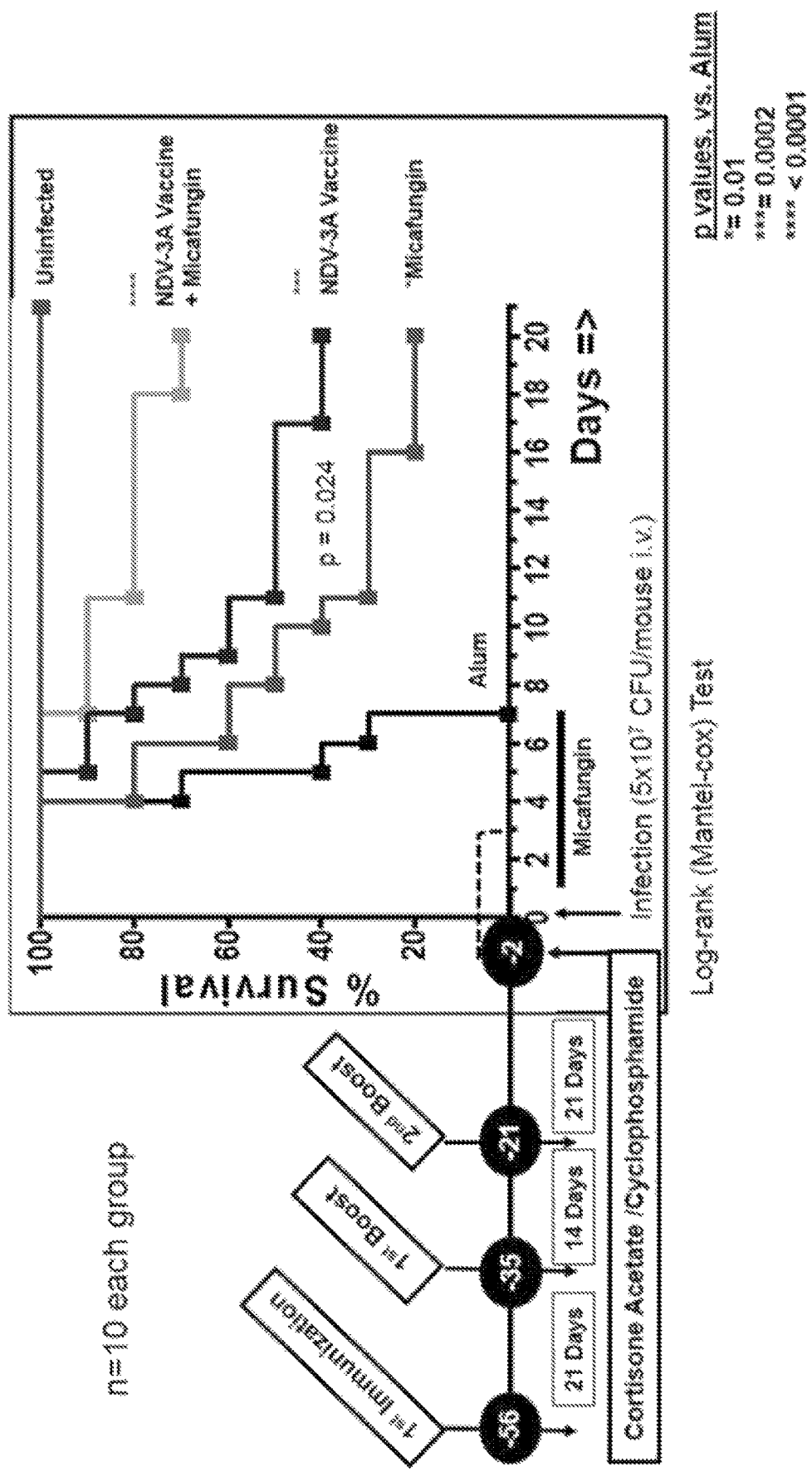

FIG. 11 is a graph showing survival of *C. auris* infected mice that have been vaccinated with NDV-3A and treated with the antifungal drug micafungin (0.25 mg/kg body weight). 300 µg Als3-2 protein formulated with 200 µg Alum was subcutaneously administered to each mouse indicated as "NDV-3A vaccine." 200 µg Alum alone (Alum) was used as a control.

Figure 12A:
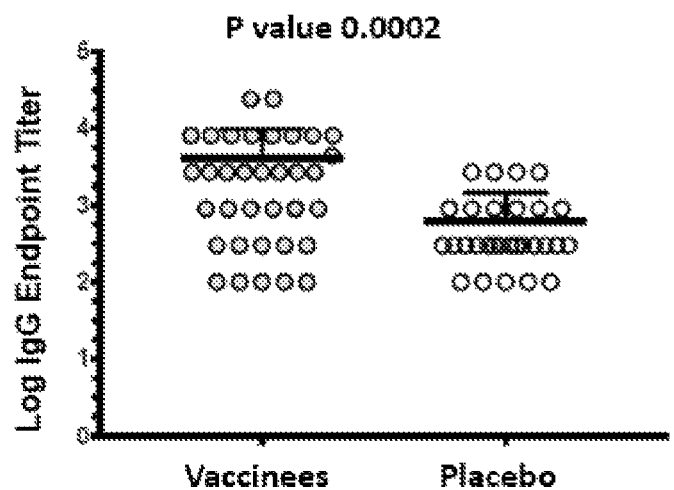

FIG. 12A is a graph showing cross-reactive antibodies identified in NDV-3A vaccinated versus placebo women by ELISA against *C. auris* lysate supernatant.

Figure 12B:
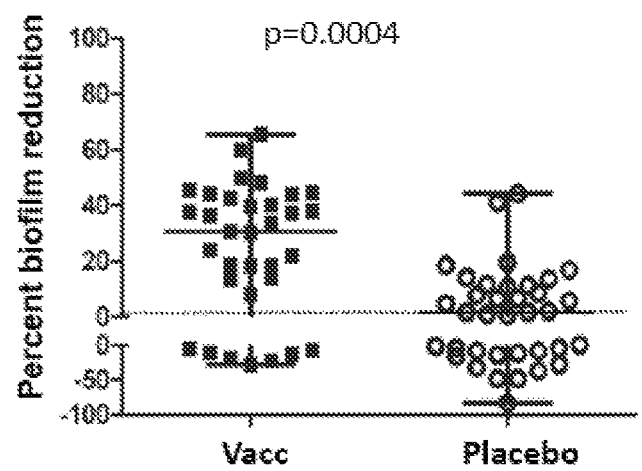

FIG. 12B is a graph quantifying reduction in biofilm formation by *C. auris* evaluated in NDV-3A vaccinated versus placebo women.

DETAILED DESCRIPTION

We have surprisingly discovered that polypeptides and fragments derived from the *Candida albicans* agglutinin-like sequence 3 (Als3) protein and antibodies or antigen-binding fragments thereof that bind these polypeptides and fragments promote treatment of and confer resistance against *C. auris* infection. Als3 is a protein normally expressed on the cell surface of the hyphal form of *C. albicans*. *C. auris* does not exhibit a hyphal form, nor is it known to express an Als3 protein. Nonetheless, we discovered that *C. auris* has two previously uncharacterized surface proteins with homology to Als3 that cross-react with anti-Als3 antibodies. Consequently, targeting *C. auris* with anti-Als3 antibodies or antigen-binding fragments thereof provides protection against infection and/or colonization of this yeast species. Disclosed herein are compositions and methods for treating and immunizing against *C. auris* infection and colonization. Als3 protein-containing compositions may be administered as immunogenic compositions and vaccines to human subjects to treat, prevent, or reduce the risk of a *C. auris* infection. Similarly, compositions containing anti-Als3 antibodies and antigen-binding fragments thereof may be administered as immunotherapy compositions to human subjects to treat or reduce the risk of a *C. auris* infection.

Patient Selection

The compositions and methods described herein can be used to treat a subject (e.g., a human) that is at risk of *C. auris* infection or prone to a *C. auris* infection (e.g., due to a history of past infection, has been exposed to, or is suspected of being exposed to *C. auris*), or a subject with (or suspected of having) an active *C. auris* infection. For example, a patient with a compromised immune system, a comorbidity, or a risk factor is one that is susceptible to, or at greater risk of, a *C. auris* infection. Some comorbidities that increase the risk of *C. auris* infections are, for example, a bacterial infection, a fungal infection, a viral infection, and immune disorder, or diabetes. The fungal infection may be candidiasis (e.g., infection with one or more *Candida* species (e.g., *C. albicans*), e.g., other than *C. auris*), such as candidiasis infection of a mucous membrane (e.g., mouth, throat, esophagus, rectum, or vagina). The candidiasis may be vulvovaginal candidiasis (e.g., recurrent vulvovaginal candidiasis (RVVC)) or invasive candidiasis. Other risk factors for *C. auris* infection are surgery, a stay in an intensive care unit, habitation in a nursing home, use of a breathing tube or feeding tube, treatment with a broad-spectrum antibiotic or antifungal agent, or a catheter, such as a central venous catheter.

Certain patients may also be at greater risk for a *C. auris* infection. These include people who have been treated at, are being treated at, or will be treated at a hospital or health center. Furthermore, people who have worked, work at, or will work at a hospital or health center may be susceptible to infection. Elderly people (e.g., older than 50, 60, 70, 80, or 90 years old) or very young people, such as newborns, infants, or toddlers (e.g., under 3 years old) may be at increased risk due to an underdeveloped immune system or an immunocompromised immune system.

Assays for diagnosing a *C. auris* infection are known (see, e.g., Kordalewska et al., J. Clin. Microbiol. 55:2445-2452, 2017, and Leach et al., J. Clin. Microbiol. 2017) and can be used to identify a patient for treatment of the *C. auris* infection. *C. auris* can also be diagnosed by standard laboratory culture growth tests following a swab of, or collection from, a tissue suspected of being infected or containing *C.*

*auris*, or a blood sample. Molecular methods using diagnostic devices based on matrix-assisted laser desorption/ionization time-of-flight (MALDI-TOF) mass spectrometry can differentiate *C. auris* from other *Candida* species. Another method includes sequencing the D1-D2 region of the 28s rDNA or the Internal Transcribed Region (ITS) of rDNA to identify *C. auris*. *C. auris* strains can also be further tested for antifungal susceptibility to determine an appropriate course of treatment.

Methods of Treatment

The compositions and methods described herein are particularly useful for human subjects, both male and female. The methods may include first identifying a subject as having a risk factor or comorbidity, as described herein, that increases the likelihood of a *C. auris* infection or colonization. In some instances, the methods include first identifying a subject as having a *C. auris* infection or *C. auris* colonization prior to administration of a treatment described herein.

After the subject is diagnosed and/or receives a treatment, the subject can be monitored over time to track the treatment progress and monitor the subject for *C. auris* colonization and/or infection. The monitoring or identifying step may include determining a change (e.g., an increase or decrease) in *C. auris* colonization in the subject as compared to *C. auris* colonization in the subject prior to administration of the treatment. The monitoring or identifying step may involve taking a sample from the subject, such as with a swab of the skin or a mucous membrane of the subject. The mucous membrane may be from the mouth, throat, esophagus, rectum, or vagina of the subject. Then, the contents of the skin swab can be cultured or analyzed to identify the presence of, or progression of, the infection.

The compositions and methods may reduce *C. auris* colonization or infection by about 10%, 20%, 30%, 40%, 50%, 60%, 70%, 80%, 85%, or 90%, or substantially eliminate colonization or infection. Furthermore, the compositions and methods described herein may be useful for inhibiting or reducing *C. auris* biofilm formation. For example, the compositions and methods may reduce or inhibit biofilm formation by about 10%, 20%, 30%, 40%, 50%, 60%, 70%, 80%, 85%, or 90%, or substantially eliminate biofilm formation. In general, the compositions and methods described herein may increase the probability of survival of the subject as compared to a subject that does not receive the treatment. The compositions and methods may reduce the number of days of active *C. auris* infection in the subject (e.g., by 1, 2, 3, 4, 5, 6, 7, 8, 9, 10, 20, 30, 40, 50, or more days), the number of days of hospitalization of the subject (e.g., by 1, 2, 3, 4, 5, 6, 7, 8, 9, 10, 20, 30, 40, 50, or more days), the number of days the subject requires antifungal therapy (e.g., by 1, 2, 3, 4, 5, 6, 7, 8, 9, 10, 20, 30, 40, 50, or more days), and/or the dose of antifungal therapy needed by the subject, e.g., each relative to an untreated subject.

Polypeptides for Immunogenic Compositions and Vaccines

*C. Albicans* Als3 is natively expressed as a 1119 amino acid pre-protein, which has the following amino acid sequence:

```
                                          (SEQ ID NO: 1)
  1 MLQQYTLLLIYLSVATAKTI TGVFNSFNSLTWSNAATYNY

KGPGTPTWNAVLGWSLDGTS

61 ASPGDTFTLNMPCVFKFTTS QTSVDLTAHGVKYATCQFQA

GEEFMTFSTLTCTVSNTLTP

121 SIKALGTVTLPLAFNVGGTG SSVDLEDSKCFTAGTNTVTF

NDGGKKISINVDFERSNVDP

181 KGYLTDSRVIPSLNKVSTLF VAPQCANGYTSGTMGFANTY

GDVQIDCSNIHVGITKGLND

241 WNYPVSSESFSYTKTCSSNG IFITYKNVPAGYRPFVDAYI

SATDVNSYTLSYANEYTCAG

301 GYWQRAPFTLRWTGYRNSDA GSNGIVIVATTRTVTDSTTA

VTTLPFDPNRDKTKTIEILK

361 PIPTTTITTSYVGVTTSYST KTAPIGETATVIVDIPYHTT

TTVTSKWTGTITSTTTHTNP

421 TOSIDTVIVQVPSPNPTVTT TEYWSQSFATTTTITGPPGN

TDTVLIREPPNHTVTTTEYW

481 SESYTTTSTFTAPPGGTDSV IIKEPPNPTVTTTEYWSESY

TTTSTFTAPPGGTDSVIIKE

541 PPNHTVTTTEYWSQSYTTTT TVTAPPGGTDTVLVREPPNH

TVTTTEYWSQSYTTTTTVIA

601 PPGGTDSVIIREPPNPTVTT TEYWSQSYATTTTITAPPGE

TDTVLIREPPNHTVTTTEYW

661 SQSYATTTTITAPPGETDTV LIREPPNHTVTTTEYWSQSF

ATTTTVTAPPGGTDTVIIRE

721 PPNHTVTTTEYWSQSYATTT TITAPPGETDTVLIREPPNH

TVTTTEYWSQSYATTTTIIA

781 PPGETDTVLIREPPNPTVTT TEYWSQSYTTATTVTAPPGG

TDTVIIYDTMSSSEISSFSR

841 PHYTNHTTLWSTTWVIETKT ITETSCEGDKGCSWVSVSTR

IVTIPNNIETPMVTNTVDST

901 TTESTSQSPSGIFSESGVSV ETESSTVTTAQTNPSVPTTE

SEVVFTTKGNNENGPYESPS

961 TNVKSSMDENSEFTTSTAAS TSTDIENETIATTGSVEASS

PIISSSADETTTVTTTAEST

1021 SVIEQPTNNNGGGKAPSATS SPSTTTTANNDSVITGTTST

NQSQSQSQYNSDTQQTTLSQ

1081 QMTSSLVSLHMLTTFDGSGS VIQHSTWLCGLITLLSLFI.
```

This protein includes an N-terminal signal sequence of 17 amino acids (underlined above), which is cleaved during production of the mature protein.

One of skill in the art would appreciate that Als3 is a surface expressed, membrane-bound protein and, thus, includes a hydrophobic transmembrane domain. Therefore, robust expression of the full length protein may be difficult to achieve in order to obtain large quantities of the protein to produce a useful yield for the creation of an immunogenic or vaccine composition. Accordingly, fragments of Als3 can be produced, which may be expressed at a higher yield than the native protein. Als3 polypeptides include, e.g., the Als3-2 fragment, which is a 416 amino acid N-terminal fragment that lacks the signal sequence has the following amino acid sequence:

(SEQ ID NO: 2)

```
KTITGVFNSF NSLTWSNAAT YNYKGPOTPT WNAVLGWSLD GTSASPGDTF TLNMPCVFKF  60
TTSQTSVDLT AHGVKYATCQ FQAGEEFMTF STLTCTVSNT LTPSIKALGT VTLPLAFNVG 120
GTGSSVDLED SKCFTAGTNT VTFNDGOKKI SINVDFERSN VDPKGYLTDS RVIPSLNKVS 180
TLFVAPQCAN GYTSGTMGFA NTYGDVQIDC SNIHVGITKG LNDWNYPVSS ESFSYTKTCS 240
SNGIFITYKN VPAGYRPFVD AYISATDVNS YTLSYANEYT CAGGYWQRAP FTLRWTGYRN 300
SDAGSNGIVI VATTRTVTDS TTAVTTLPFD PNRDKTKTIE ILKPIPTTTI TTSYVGVTTS 360
YLTKTAPIGE TATVIVDIPY HTTTTVTSKW TGTITSTTTH TNPTDSIDTV IVQVPL.    416
```

Another Als3 polypeptide fragment is the Als3-1 fragment, which is similar to Als3-2, but is a 425 amino acid fragment that contains a 6×-His tag and a three amino acid GIQ linker at the N-terminus to facilitate protein purification. The amino acid sequence of Als3-1 is:

(SEQ ID NO: 3)

```
HHHHHHGIQK TITGVFNSFN SLTWSNAATY NYKGPOTPTW NAVLOWSLDG TSASPGDTFT  60
LNMPCVFKFT TSQTSVDLTA HGVKYATCQF QAGEEFMTFS TLTCTVSNTL TPSIKALGTV 120
TLPLAFNVGG TGSSVDLEDS KCFTAGTNTV TFNDGOKKIS INVDFERSNV DPKGYLTDSR 180
VIPSLNKVST LFVAPQCANG YTSGTMGFAN TYGDVQIDCS NIHVGITKGL NDWNYPVSSE 240
SFSYTKTCSS NGIFITYKNV PAGYRPFVDA YISATDVNSY TLSYANEYTC AGGYWQRAPF 300
TLRWTGYRNS DAGSNGIVIV ATTRTVTDST TAVTTLPFDP NRDKTKTIEI LKPIPTTTIT 360
TSYVGVTTSY LTKTAPIGET ATVIVDIPYH TTTTVTSKWT GTITSTTTHT NPTDSIDTVI 420
VQVPL.                                                            425
```

Another Als3 polypeptide fragment is a 307 amino acid fragment corresponding to residues 18-324 of Als3 and designated as Als3 (18-324). The amino acid sequence of Als3 (18-324) is:

(SEQ ID NO: 4)

```
KTITGVFNSF NSLTWSNAAT YNYKGPGTPT WNAVLGWSLD
GTSASPGDTF TLNMPCVFKF TTSQTSVDLT AHGVKYATCQ
FQAGEEFMTF STLTCTVSNT LTPSIKALGT VTLPLAFNVG
GTGSSVDLED SKCFTAGTNT VTFNDGOKKI SINVDFERSN
VDPKGYLTDS RVIPSLNKVS TLFVAPQCAN GYTSGTMGFA
NTYGDVQIDC SNIHVGITKG LNDWNYPVSS ESFSYTKTCS
SNGIFITYKN VPAGYRPFVD AYISATDVNS YTLSYANEYT
CAGGYWQRAP FTLRWTGYRN SDAGSNG.
```

A 108 amino acid Als3 fragment, designated as Als3 Ser/Thr-rich sequence, which contains residues 325-432, has the following amino acid sequence:

(SEQ ID NO: 5)

```
IVIVATTRTVTDSTTAVTTLPFDPNRDKTKTIEILKPIPTTTIT
TSYVGVTTSYSTKTAPIGETATVIVDIPYHTTTTVTSKWTGTIT
STTTHTNPTDSIDTVIVQVP.
```

Exemplary polypeptides that may be used in conjunction with the compositions and methods as described herein include any polypeptide, fragment, homolog, or ortholog thereof of an Als3 polypeptide, such as the polypeptide fragments described above. Furthermore, fragments and variants of the Als3 homologs or orthologs may be used.

The *C. auris* genome is not believed to contain an Als3 gene, although genes encoding hypothetical proteins with homology to *C. albicans* Als3 have been identified. One protein is designated as *C. auris* hypothetical protein QG37_06265 (Genbank Accession No. XP 018167572.1) and has the following 861 amino acid sequence:

(SEQ ID NO: 6)

```
  1 MKIISLLWCL ALLYGNALAA PQTGVFTSID SLTPFDVAWP
    MMPGWDATVS WHINSSMEMK
 61 DGDTFFLRIP FVIEFNTDES SIQMSDGTNT FANCVLTPGE
    NLVPYSEVKC TATTQVEDVQ
121 SSSGTITFPI VFNAGFSAQE LDLKAANHWR TGSNTLEWTD
    GSNTLTHPIT FVGGTMSAFN
181 GRPKRGILDQ RSFVSTNTIR QFLMGPLCHS SDMSGELSIE
    NLLEEAPFDC DSITTAMSNQ
```

```
241 INAWYFPQTA DEAEATIVSC SAAGVNVAFS NLPAGFRPYI
    NIDATKKIAV SEIDNIYHYN
301 FTCNGAELSD SIFAAWDQFF SDDTEEDDTL TQVVVTTATD
    PGITATSIAT HTGTDANTIV
361 VNVPISESTV IVTGTNSIAT TKTFTSSGTR IVSIDTPIPT
    STITSTWTES VTSTYTVPAS
421 PGVTASVIVE VPIPTTTITQ TWTGMETMTQ TLPAEIGETQ
    SVIVNIPDST TIMSSNEATS
481 EQTMSLSVDT IPTSLMNSST SSGASLSEEI STQETSLSSQ
    SSDESVSQTE SYTASDPSPP
541 VSSSFLNTSS SKIGSQLLLS SQSDPVSTSE MAPQSGISSY
    ITSWIGSITV PSSLSAETDS
601 AQETSYHTTK SPTDNSASEN VYLTESKKTE NTDTKASHSV
    ISTSGTSDIN DSSSDAYIDP
661 SISTTTIGVP SISVNWNSSF VITTLVSETT CISSTPKTVS
    ETLDIQDLFS TCKEASAKTN
721 NEGSLKASKL SKSTSKIDTK VIFPTSEPDF IASTSSYWSQ
    DIQSSNQFNI MTSPDISLAQ
781 SGPTELALAR CTSANCGTQT NSKGQNPNVA TSLMSISNSD
    APAVSPSSSQ LPSVLTYSGI
841 SSTLKVSGIL AMFVSLTQIL F.
```

A second protein, designated as *C. auris* hypothetical protein QG37_05979 (Genbank Accession No. XP_018167307.1), has the following 714 amino acid sequence:

```
                                          (SEQ ID NO: 7)
  1 MLAYTIASPA AIKPESDVEK SEVKNTEDEN TSEAQDDSAN
    PEVQLPEPLT METFDDFTSQ
 61 HITFVEFFSP YCHHCQALAP KWEQAFRETY EQQQKTGLHM
    RQVNCVESGD LCDREVVPYW
121 PNMRVYVPER DEKGEKTGKG KLVDSFPRAL KQTPKNLKKF
    MMNSLAEYAD GTISMPSSSE
181 LLNTDSMLNI VAGEMNEPWF VGMFSSSNEE WEKGTFSRSC
    MDCLRIKSDW DRLSNLIQSS
241 TKSGHLNCKS NPTLCEKLGY PELSSDMRQA PKFAMFLPSK
    VGRIRFDYND IVDVKKMKAW
301 ISRLAINSQY EMATAGHLED LDLFVTEKPS SPLQVELPLN
    TKVGLVFAFE KNKLTKEDKA
361 ILPHLLEMIT DLPFNVRLYA SHSVKFEETL EYQSKGLIDF
    VKTDPTLEEV TYSRPLHIAT
421 TLTKKPTLYL FKENSMIPTV YQNYAPEDMR DPEKIKAWVM
    KNIYPLFDEL TPELLKWYFN
481 TKDKRNDKVV VTFVDONDDK HLKEALYNVS LVAHEYTLLK
    KQYYFKALQD ERSSKWQKIT
541 ELREKGAKSS EVIKAMKEYV PHLFDHNDAL FTYVNLREYP
    RFAKDIGWDI DGEGYKPGDT
601 IIVNKNTKYY YDRTLTGEKL TIEPSKLRPV LLHLLDPQLT
    KDAKVVGFSP RLAASPFTGY
661 LRFMDQIYQH GIVGIILFFI GVFLFLKMAL RFMKRGKHTS
    RSRGIIGNVA PKHD.
```

Polypeptides comprising any protein, fragment, or variant or modified version of any one of SEQ ID NOs: 1-7 can be prepared as an immunogenic composition or vaccine and used to treat or immunize against a *C. auris* infection in a subject (e.g., a human subject). The polypeptides of the invention may have, for example, at least 70%, 75%, 80%, 85%, 90%, 95%, 97%, 98%, 99%, or 100% sequence identity with any one of SEQ ID NOs: 1-7 or may have at least 70%, 75%, 80%, 85%, 90%, 95%, 97%, 98%, 99%, or 100% sequence identity with any fragment thereof of SEQ ID NOs: 1-7.

The full length native Als3 protein of SEQ ID NO: 1 consists of 1119 amino acids. Thus, fragments of Als3 that may be used to prepare compositions for use in the methods described herein include, e.g., fragments of Als3 that are fewer than 1119, 1118, 1117, 1116, 1115, 1114, 1113, 1112, 1111, 1110, 1100, 1090, 1080, 1070, 1060, 1050, 1040, 1030, 1020, 1010, 1000, 990, 980, 970, 960, 950, 940, 930, 920, 910, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids in length.

The Als3 polypeptide of SEQ ID NO: 1 could also be truncated at either the N-terminus or the C-terminus, or at both termini, to produce an immunogenic fragment, e.g., for use in the methods described herein. For example, the N-terminus, the C-terminus, or both the N-terminus and the C-terminus may be truncated by at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, or 1100 amino acids.

The *C. auris* Als3 homolog of SEQ ID NO: 6 contains 861 amino acids. Thus, fragments of SEQ ID NO: 6 can be used to produce an immunogenic composition or vaccine and used to treat or immunize against a *C. auris* infection in a subject (e.g., a human subject). Such fragments include, e.g., fragments of SEQ ID NO: 6 that are fewer than 861, 860, 859, 858, 857, 856, 855, 854, 853, 852, 851, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids in length. The N-terminus, the C-terminus, or both the N-terminus and C-terminus may be truncated by 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, or 850 acids.

The *C. auris* Als3 homolog of SEQ ID NO: 7 consists of 714 amino acids. Thus, fragments of SEQ ID NO: 7 can be used to produce an immunogenic composition or vaccine and used to treat or immunize against a *C. auris* infection in a subject (e.g., a human subject). Such fragments of SEQ ID NO: 7 include fragments of SEQ ID NO: 7 that are fewer than 714, 713, 712, 711, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids in length. The N-terminus, the C-terminus, or both the N-terminus and C-terminus may be truncated by 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, or 710 amino acids.

In some instances, a polypeptide as described herein (e.g., the polypeptides of SEQ ID NOs: 1-7 or fragments thereof) may comprise a modification (e.g., chemical modification, e.g., post-translational modification). Preferably, the modification does not substantially reduce the immunogenicity of the polypeptide. The modified polypeptide (e.g., the polypeptides of SEQ ID NOs: 1-7) may have or may optimize a characteristic of the polypeptide, such as in vivo stability, bioavailability, toxicity, immunological activity, immunological identity, or conjugation properties.

A polypeptide as described herein (e.g., the polypeptides of SEQ ID NOs: 1-7) can also include one or more amino acid insertions, deletions, or substitutions in the polypeptide sequence. For example, the addition of one or more residues (e.g., cysteine residues) to the N- or C-terminus of any of the polypeptides described herein (e.g., the polypeptides of SEQ ID NOs: 1-7) can facilitate conjugation of these polypeptides with a chemical moiety or fusion partner. Additional (e.g., 1, 2, 3, 4, 5, 6, and 7, 8, 9, 10, or more) residues may also be present at the N- or C-termini that not part of the native peptide sequence (e.g., the sequences of SEQ ID NOs: 1-7). Amino acid substitutions can be conservative (i.e., in which a residue is replaced by another with similar chemical properties) or non-conservative (i.e., in which a residue is replaced by an amino acid with different chemical properties).

Als3 polypeptides (e.g., the polypeptides of SEQ ID NOs: 1-5 and fragments thereof) and orthologs thereof (e.g., the polypeptides of SEQ ID NOs: 6-7 and fragments thereof) may be made synthetically, e.g., using methods known in the art, and can include, e.g., substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline.

The polypeptides described herein (e.g., the polypeptides of SEQ ID NOs: 1-7 and fragments, variants, and homologs thereof) can be obtained by chemical synthesis using a commercially available automated peptide synthesizer. The synthesized protein or polypeptide can be precipitated and further purified, for example by high performance liquid chromatography (HPLC). Alternatively, the proteins and polypeptides can be obtained by recombinant methods that are well-known in the art (e.g., expression in *S. cerevisiae, E. coli*, CHO cells, or insect cells).

The polypeptides described herein (e.g., the polypeptides of SEQ ID NOs: 1-7 and fragments, variants, and homologs thereof) may be conjugated or fused with another moiety (e.g., a heterologous protein or chemical moiety) to improve its physical properties (e.g., stability, immunogenicity, expression, purity).

Antibodies and Antigen-Binding Fragments

Also featured are anti-Als3 antibodies and antigen binding fragments thereof. These antibodies may specifically bind an epitope present in an Als3 polypeptide or fragment thereof, such as the polypeptides of SEQ ID NOs: 1-5. The invention also features antibodies and antigen-binding fragments thereof directed to homologs or orthologs of Als3 and fragments of said homologs or orthologs, such as the *C. auris* Als3 orthologs of SEQ ID NOs: 6-7. The antibodies may bind any epitope present in an Als3 homolog or ortholog or a fragment or variant thereof (e.g., fragment or variant of SEQ ID NOs: 6-7).

The antibody may be a polyclonal, monoclonal, genetically engineered, and otherwise modified form of antibody, including but not limited to a chimeric antibody, human antibody, murine antibody, humanized antibody, heteroconjugate antibody (e.g., bi- tri- and quad-specific antibody, diabody, triabody, and tetrabody), and antigen binding fragments of such antibodies, including, for example, Fab', F(ab')2, Fab, Fv, rIgG, and scFv fragments. A monoclonal antibody (mAb) is meant to include both intact molecules, as well as antibody fragments (including, for example, Fab and F(ab')2 fragments) that are capable of specifically binding to a target protein. Fab and F(ab')2 fragments refer to antibody fragments that lack the Fc fragment of an intact antibody.

The antibody can be generated using an epitope present within any one of SEQ ID NOs: 1-7 or the antibody can be one that cross-reacts with an epitope present within any one of SEQ ID NOs: 1-7. The antibody may bind an epitope (e.g., an epitope present in any one of SEQ ID NOs: 1-7) with a $K_D$ of less than 100 nM (e.g., 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 900 μM, 800 μM, 700 μM, 600 μM, 500 μM, 400 μM, 300 μM, 200 μM, 100 μM, or less).

An antigen-binding fragment refers to one or more fragments of an antibody that retain the ability to specifically bind to a target antigen (e.g., an Als3 polypeptide or a polypeptide of any one of SEQ ID NOs: 1-7 or a fragment, variant, or homolog thereof). The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of antigen-binding fragments include, but are not limited to: a Fab fragment, a monovalent fragment consisting of the $V_L$, $V_H$, $C_L$, and $C_H 1$ domains, a $F(ab')_2$ fragment, a bivalent fragment comprising two Fab fragments linked by a disulfide bridge at the hinge region, a Fd fragment consisting of the $V_H$ and $C_H 1$ domains, a Fv fragment consisting of the $V_L$ and $V_H$ domains of a single arm of an antibody, a dAb including $V_H$ and $V_L$ domains, a dAb fragment that consists of a $V_H$ domain (see, e.g., Ward et al., Nature 341:544-546, 1989), a dAb which consists of a $V_H$ or a $V_L$ domain, an isolated complementarity determining region (CDR), and a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al., *Science* 242: 423-426, 1988 and Huston et al., *Proc. Natl. Acad. Sci. USA* 85: 5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

Monoclonal antibodies (e.g., anti-Als3 antibodies) may be made, for example, by using the hybridoma method first described by Kohler et al., Nature 256:495, 1975, or may be made by recombinant DNA methods (see, e.g., U.S. Pat. No. 4,816,567). In the hybridoma method, a mouse or other appropriate host animal, such as a hamster or macaque monkey, is immunized, e.g., using a polypeptide described herein (e.g., the polypeptides of any one of SEQ ID NOs: 1-7), to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, Academic Press, 1986). The antibody may also be made in an animal model that has been genetically modified to product human antibodies.

Formulations and Carriers

The polypeptides or fragments described herein (e.g., the polypeptides of any one of SEQ ID NOs: 1-7) and the antibodies or antigen-binding fragments thereof (e.g., antibodies and antigen-binding fragments thereof directed against an epitope present in any one of SEQ ID NOs: 1-7) may be formulated as a pharmaceutical composition for administration to a subject (e.g., a human subject).

Pharmaceutical compositions can be prepared using standard pharmaceutical formulation chemistries and methodologies that are readily available to the reasonably skilled artisan. For example, polypeptides and antibodies or antigen-binding fragments thereof described herein (e.g., the polypeptides of any one of SEQ ID NOs: 1-7 or fragments thereof, and antibodies or antigen-binding fragments thereof that specifically bind to an epitope within any one of SEQ ID NOs: 1-7) can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids, such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions (e.g., pharmaceutical compositions comprising an Als3 polypeptide or fragment or homolog thereof, e.g., of any one of SEQ ID NOs: 1-7, or an antibody or antigen-binding fragment thereof that specifically binds an epitope present in any one of SEQ ID NOs: 1-7) may be prepared, packaged, or sold in a form suitable for bolus administration or for continuous administration. Injectable compositions may be prepared, packaged, or sold in unit dosage form, such as in ampoules or in multi-dose containers containing a preservative.

Compositions may include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (e.g., a powder or granules) form for reconstitution with a suitable vehicle (e.g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions that are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the polypeptides or fragments thereof and/ or the antibodies or antigen-binding fragments thereof described herein (e.g., the polypeptides of any one of SEQ ID NOs: 1-7 and fragments thereof and antibodies or antigen-binding fragments thereof that bind to an epitope within any one of SEQ ID NOs: 1-7) may be encapsulated, adsorbed to, or associated with particulate carriers. Suitable particulate carriers include those derived from polymethyl methacrylate polymers, as well as PLG microparticles derived from poly(lactides) and poly(lactide-co-glycolides). See, e.g., Jeffery et al. (1993) *Pharm. Res.* 10:362-368. Other particulate systems and polymers can also be used, for example, polymers such as polylysine, polyarginine, polyornithine, spermine, spermidine, as well as conjugates of these molecules.

The anti-Als3 antibodies or fragments thereof (e.g., antibodies that specifically bind to an epitope within any one of SEQ ID NOs: 1-7) may be formulated as a composition with an excipient selected from a buffer, salt, surfactant, polyol/disaccharide/polysaccharide, amino acid, and/or antioxidant. For example, the composition may contain a buffer that keeps pH levels between 4.7 and 7.4, such as acetate, citrate, histidine, succinate, phosphate, and hydroxymethylaminomethane (Tris). If present, a surfactant may be selected from one or more of polysorbate 80 (Tween 80), polysorbate 20 (Tween 20), and poloxamer 188. Among those, 72% used polysorbate 80. For lyophilized or liquid compositions, one or a mixture of polyol/disaccharide/polysaccharide (e.g., mannitol, sorbitol, sucrose, trehalose, and dextran 40) may be present. The composition may also include sodium chloride (NaCl). Amino acids that may be included in an antibody formulation include, e.g., glycine and arginine. Finally, antioxidants that may be included in the compositions include ascorbic acid, methionine, and ethylenediaminetetraacetic acid (EDTA).

Adjuvants

Substances that stimulate the immune response, e.g., adjuvants, may be included in the compositions that comprise polypeptides (e.g., Als3 polypeptides). Adjuvants are substances that cause and/or increase stimulation of the immune system. In this context, an adjuvant is used to enhance an immune response to one or more immunogenic peptides (e.g., one or more of the Als3 polypeptides described herein). An adjuvant may be administered to a subject before, in combination with, or after administration of an immunogenic composition, an Als3 peptide, fragment or homolog thereof, or a vaccine described herein. Examples of chemical compounds used as adjuvants include, but are not limited to, aluminum compounds (e.g., alum, aluminum hydroxide, aluminum phosphate, ALHYDROGEL®, ADJU-PHOS®), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, Freund's adjuvant, and co-stimulatory factors.

Immunogenic and Vaccine Formulations

The polypeptides or fragments described herein (e.g., the polypeptides of any one of SEQ ID NOs: 1-7 or fragments thereof) may be formulated as an immunogenic composition or a vaccine. The formulated compositions will include an amount of one or more polypeptides described herein (e.g., the polypeptides of any one of SEQ ID NOs: 1-7 or fragments thereof) that is sufficient to mount an immunological response, e.g., as determined by antibody titer in the subject, such as by ELISA, antibody subclass determination, an opsonophagocytosis assay (see, e.g., Dwyer and Gadjeva, *Methods Mol. Biol.* 1100:373-379, 2014), or the presence of cellular anamnesis, e.g., CD4+ and/or CD8+ cellular responses, e.g., using flow cytometry or MHC tetramer staining. An immunogenic amount can be readily determined by one of skill in the art. The compositions may contain from about 0.1% to about 99.9% of the polypeptides (e.g., of SEQ ID NOs: 1-7 or a fragment thereof), and can be administered to the subject.

Immunogenic and vaccine compositions can include a mixture of distinct polypeptides as described herein. For example, immunogenic compositions or vaccines may include, e.g., 1, 2, 3, 4, 5, 6, 7, 8, 9, 10, or more distinct polypeptides as described herein, e.g., containing or consisting of the amino acid sequences of SEQ ID NOs: 1, 2, 3, 4, 5, 6, or 7, or a variant sequence thereof having up multiple (e.g., 1, 2, 3, 4, 5, 6, 7, 8, 9, 10 or more) substitutions (e.g., conservative substitutions), deletions, or additions to the amino acid sequence of any one of SEQ ID NOs:1, 2, 3, 4, 5, 6, or 7.

Als3 polypeptides (e.g., the polypeptides of any one of SEQ ID NOs: 1-7), optionally in combination with an adjuvant (e.g., aluminum hydroxide; also see examples described above), can be formulated in compositions including, for example, a buffer and a salt. Such compositions can include, for example, sodium phosphate, sodium citrate, histidine, or sodium succinate (2-20 mM, e.g., 5-15 mM or 10 mM), pH 6.0-8.0 (e.g., pH 6.5-7.5 or pH 7.0), as well as sodium chloride (100-300 mM, e.g., 100-200 mM or 154 mM.

A specific example of a vaccine formulation that can be used in the invention is NDV-3, which includes Als3-1 (SEQ ID NO: 3) formulated in 10 mM sodium phosphate, pH 7.0, and 154 mM sodium chloride. Another example is NDV-3A, which includes Als3-2 (SEQ ID NO:2) formulated in 10 mM sodium phosphate, pH 6.5, and 154 mM sodium chloride. The NDV-3 and NDV-3A vaccines can optionally be filled in 2 mL glass vials with a 0.7 mL volume containing 600 µg Als3-1 (or Als3-2)/mL, 1.0 mg Al/mL as aluminum hydroxide and phosphate-buffered saline. When withdrawn from the vial with a needle and syringe for injection, approximately 0.5 mL can be injected (e.g., by the intramuscular route), resulting in a delivered dose of 300 µg of Als3-1 (or Als3-2).

Dosage and Administration

The compositions described herein (e.g., the polypeptides of SEQ ID NOs: 1-7 or fragments thereof or antibodies or fragments thereof that specifically bind to an epitope within any one of SEQ ID NOs: 1-7) can be administered to a subject (e.g., a human patient) in a variety of ways. The compositions may contain a polypeptide or fragment thereof or an antibody or fragment thereof as the sole active agent or in combination with one or more additional active agents. Furthermore, the severity of the infection to be treated may affect the dosage administered, the route of administration, or the frequency of administration. The dosage regimen may be determined by the clinical indication being addressed, as well as by various patient variables (e.g., weight, age, sex) and clinical presentation (e.g., extent or severity of infection). The compositions may be administered orally, buccally, sublingually, parenterally, intravenously, subcutaneously, intramedullary, intranasally, as a suppository, using a flash formulation, topically, intradermally, intramuscularly, via pulmonary delivery, via intra-arterial injection, intrathecally, via an infusion (e.g., continuous infusion or Bolus infusion), or via a mucosal route. Furthermore, it is understood that the dosage(s) may be continuously given or divided into multiple dosages given over time. The composition may be administered, for example, one or more times every hour, day, week, month, or year.

In general, the dosage of a pharmaceutical composition described herein, or an active agent in a pharmaceutical composition described herein (e.g., the polypeptides of any one of SEQ ID NOs: 1-7 or fragments thereof and antibodies that bind an epitope within any one of SEQ ID NOs: 1-7), may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The Als3 polypeptide or anti-Als3 antibody, or fragments thereof, may also be administered in a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg).

Preferred embodiments for antibody administration (e.g., antibodies or fragments thereof that specifically bind to an epitope present in any one of SEQ ID NOs: 1-7) include infusions, such as continuous or bolus infusions. About 0.5 g to about 5 g of the anti-Als3 antibody may be administered. The anti-Als3 antibody may be administered in a suitable volume of about 1 mL to about 1 L (e.g., 10 mL-1 L, e.g., 900 mL, 800 mL, 700 mL, 600 mL, 500 mL, 400 mL, 300 mL, 200 mL, 100 mL, 50 mL, 10 mL, 5 mL, 4 mL, 3 mL, 2 mL, 1 mL, or less). The anti-Als3 antibody may be administered at a dosage of about 1 mg/kg to about 20 mg/kg. The dose may also be administered as a dose per mass or weight of the patient per unit day (e.g., 0.1-10 mg/kg/day).

Immunogenic compositions and vaccines comprising the polypeptides as described herein (e.g., the polypeptides of any one of SEQ ID NOs: 1-7 or fragments thereof) can be administered in multiple doses (e.g., 2, 3, 4, 5, or more), such as a primary dose and one or more (e.g., 2, 3, 4, 5, or more) subsequent booster doses. For example, an initial dose of the polypeptide may be administered, and a second dose may be administered between 1 and 100 days (e.g., 2 days, 3 days, 4 days, 5 days, 10 days, 15 days, 20 days, 25 days, 30 days, 35 days, 40 days, or 45 days, 50 days, 60 days, 70 days, 80 days, 90 days) later. The second dose may be administered about 7 to 90 days, 1 to 50 days, 21 to 60 days, or about 22 days after the first dose. In some preferred embodiments, about 5 µg to about 5 mg (e.g., about 10-600 µg, 20-300 µg, 30-300 µg, 30-90 µg. or 200-300 µg) of an Als3 polypeptide or fragment or homolog thereof (e.g., of any one of SEQ ID NOs: 1-7) is administered. These dosages may be administered in a suitable volume of 0.1 mL to about 1 L (e.g., 2 mL, 1 mL, 0.75 mL, 0.5 mL, or 0.25 mL, or less).

Combination Therapies

The methods described herein of treatment of or immunization against a *C. auris* infection may include administration of combination therapies comprising two or more pharmaceutical agents (e.g., an Als3 polypeptide (e.g., of any one of SEQ ID NOs: 1-5) or an anti-Als3 antibody or fragment thereof and an antifungal drug). The two or more agents may be administered sequentially (in any order, and including at substantially the same time) or as an admixture. For example, the agents may be administered within about 1 month, 2 weeks, 1 week, 1 day, 12 hours, 6 hours, or 1 hour of each other, or at substantially the same time. The two or more agents may be administered in the same formulation or as separate formulations.

The antifungal drug may be an azole, a polyene, an allylamine, an echinocandin, a lanosterol demethylase inhibitor, benzoic acid, ciclopirox oamine, enfumafungin, 5-flucytosin, griseofulvin, haloprogin, tolnaftate, aminocandin, chlordantoin, chlorphenesin, nifuroxime, undecylenic acid, or crystal violet. The azole may be a triazole, an imidazole, or a thiazole. The triazole may be fluconazole, albaconazole, efinaconazole, epoxiconazole, isavuconazole, itraconazole, posaconazole, propiconazole, ravuconazole, terconazole, or voriconazole. The imidazole may be bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, or tioconazole. The thiazole may be abafungin. The polyene may be amphotericin B, candicidin, filipin, hamycin, natamycin, nystatin, or rimocidin. The allylamine may be amorolfin, butenafine, naftifine, or terbinafine. The echinocandin may be anidulafungin, biafungin, caspofungin, or micafungin. The lanosterol demethylase inhibitor may be VT-1161. Any of the antifungal drugs may be a in the form of a pharmaceutically acceptable salt or ester thereof.

Kits

Also featured are kits that can be used to carry out the methods of treatment of or immunization against a *C. auris* infection, as described herein. Kits of the invention can include one or more Als3 polypeptides or fragments or homologs thereof (e.g., any one of SEQ ID NOs: 1-7), optionally in the form of an immunogenic or vaccine composition, such as a composition containing an adjuvant (for example, aluminum hydroxide). In an example, the Als3 polypeptide or fragment or homolog thereof (e.g., any one of SEQ ID NOs: 1-7) is present in a container (e.g., a glass vial) in liquid form (e.g., in water or a buffered salt solution, such as, e.g., 10 mM sodium phosphate, pH 6.5 or 7.0, and 154 mM sodium chloride; see above for other examples of buffer and salt conditions that can be used). In another example, the Als3 polypeptide or fragment or homolog thereof (e.g., any one of SEQ ID NOs: 1-7) is present in a container (e.g., a glass vial) in lyophilized form. In this example, the kit may optionally also include a diluent (e.g., water or a buffered salt solution) for reconstitution of the lyophilized polypeptide into liquid form prior to administration. The polypeptide may also be present in another formulation, as described herein, or as is known in the art. The amount of polypeptide and, optionally, adjuvant present in the compositions of the kits can be, for example, as described above. Thus, for example, the kits can include an Als3 polypeptide or fragment or homolog thereof (e.g., any one of SEQ ID NOs: 1-7) in an amount to facilitate the administration of a dose as described herein.

Also featured are kits with an anti-Als3 antibody or antigen-binding fragment thereof, such as those described above. The anti-Als3 antibody or antigen-binding fragment thereof may be present in a composition that is formulated for administration to a subject, or the composition may be present in the kit in lyophilized form. If so, the kit may also include a diluent for reconstituting the composition containing the anti-Als3 antibody or antigen-binding fragment thereof. The composition containing the anti-Als3 antibody or antigen-binding fragment thereof may be formulated as discussed above and may be present in the kit at one of the concentrations discussed above.

In addition to the Als3 polypeptide or fragment thereof or the anti-Als3 antibody or antigen-binding fragment thereof, the kits may also include one or more antifungal agents (e.g., fluconazole, ketoconazole, butoconazole, miconazole, terconazole, tioconazole, clotrimazole, and nystatin, or any of the other antifungal agents described above). In the case of, for example, fluconazole, the kits can include one or more doses in an amount as described herein, formulated in a tablet for oral administration (e.g., the fluconazole may be present in table form at a dosage of 50, 100, or 200 mg; the tablet may also include the following inactive ingredients: microcrystalline cellulose, dibasic calcium phosphate anhydrous, povidone, croscarmellose sodium, and magnesium stearate). The kit may include a single dose of the antifungal agent (e.g., fluconazole), or 2, 3, 4, 5, 6, 7, 8, 9, or 10 doses (e.g., at least 3 doses) of the antifungal agent (e.g., fluconazole). Other agents, such as butoconazole, miconazole, terconazole, tioconazole, and clotrimazole, may be present in the kits instead of, or in addition to, fluconazole. These agents may be in the form of a cream. Alternatively, clotrimazole, miconazole, and terconazole can be present in the form of a vaginal suppository, as is known in the art. These agents can be present in single or multiple doses. The antifungal agent may be packaged in a separate container within the kit so that a user (e.g., a physician) can provide the package containing the antifungal agent to a patient, or the antifungal agent may be present as an admixture with the Als3 polypeptide or fragment thereof or the anti-Als3 antibody or antigen-binding fragment thereof.

The kit components can be provided in dosage form to facilitate administration, and can optionally include materials required for administration and/or instructions for patient treatment consistent with, for example, the methods described herein.

For example, the kit can include instructions for use, which guides the user (e.g., the physician) with respect to the administration of the Als3 vaccine (e.g., the NDV-3 or NDV-3A vaccine, e.g., at the point of care location). The kit can also include instructions guiding the physician to administer a first dose of an antifungal agent (e.g., fluconazole). These instructions, or a separate set of instructions, in the kit may guide a user (e.g., a patient) with respect to the administration of the antifungal agent, which may be separately packaged in the kit so that the antifungal agent can be given to the patient for later home administration. For example, the instructions may guide the user (e.g., the physician or patient) to administer a first dose of the antifungal agent immediately and to administer a second and subsequent doses of the antifungal agent every 12 hours, 24 hours, 36 hours, 48 hours, or 72 hours, or until the antifungal agent consumed.

The kit may be packaged in materials suitable for storage at room temperature (e.g., about 70° F. (20° C.) or in a refrigerator at a temperature of between 35° F. and 46° F. (2° C. and 8° C.).

EXAMPLES

The following examples are intended to illustrate, rather than limit, the disclosure.

Example 1. NDV-3A Vaccine Protects Neutropenic Mice from Multi-Drug Resistant *C. auris* Infection We examined the emerging multi-drug resistant (MDR) fungus *C. auris* for Als3 homologs and tested the efficacy of NDV-3A vaccination in protecting mice from hematogenously disseminated candidiasis due to *C. auris*. The NDV-3A vaccine used in this example contains the Als3 polypeptide of SEQ ID NO: 3 formulated with an aluminum hydroxide adjuvant in phosphate-buffered saline.

First, we identified homologs of Als3 in *C. auris* by blasting the Als3 sequence against the *C. auris* proteome. Two *C. auris* orthologs (hypothetical proteins QG37_06265 Genbank Accession No. XP_018167572.1; SEQ ID NO: 6 and QG37_05979 Genbank Accession No. XP 018167307.1; SEQ ID NO: 7), were identified to have 47% overall sequence identity with *C. albicans* Als3 protein (SEQ ID NO: 1). However, regions of higher sequence identities were identified in the N-terminus region believed to have the functional properties of Als3 protein. These had 72-82% overlapping sequence identity between *C. auris* proteins and Als3 (FIG. 1). These two proteins had previously been uncharacterized.

Next, we studied the in vivo efficacy of the NDV-3A vaccine by vaccinating CD-1 male mice with 300 μg of the NDV-3A vaccine via subcutaneous injection on day 0. The mice were injected with a booster dose on days 21 and 35, and the mouse sera were obtained on day 42 to test for the development of anti-Als3 antibody titers by ELISA. The sera produced from these mice were able to bind *C. auris* at high affinity as determined by flow cytometry and immunofluorescence staining (FIGS. 2-4).

We tested the ability of antisera to prevent *C. auris* virulence traits (adhesion to plastic, biofilm formation, and sensitivity to neutrophil killing. Compared to placebo sera, sera (5%) from NDV-3A vaccinated mice enhanced neutrophil killing of *C. auris* ex vivo (p=0.002) (FIG. 5) and reduced *C. auris* adhesion to plastic and biofilm formation in vitro (p=0.001) (FIG. 6).

To test the efficacy of NDV-3A vaccine, vaccinated mice were made neutropenic by cyclophosphamide (200 mg/kg) and cortisone acetate on day 47 and day 52. Mice were infected intravenously with $5 \times 10^7$ blastospores of *C. auris* on day 49. Mice were vaccinated with 300 μg NDV-3A vaccine and 200 μg alum, or just 200 μg alum. 18 days after infection, 40% of the vaccinated mice survived, as compared to 0% of the alum control (FIG. 7). 100% of the uninfected mice survived.

Next, we measured the MIC for various antifungal drugs to test their efficacy in treating *C. auris* infection. In particular, we tested fluconazole, amphotericin B, posaconazole, micafungin, caspofungin, isavuconazole, and amplyx APX001, with DMSO or no drug media used as a control (FIGS. 8A-8B). We also tested the ability of either fluconazole, caspofungin, micafungin alone or in combination with the NDV-3A vaccine to enhance survival of infected mice. Als3 vaccination in combination with fluconazole resulted in 50% survival 20 days after infection. Treatment with the Als3 vaccine alone resulted in 40% survival (FIG. 9). Als3 vaccination in combination with caspofungin resulted in 40% survival (FIG. 10). Neither fluconazole nor caspofungin treatment was antagonized by NDV-3A vaccination. Finally, Als3 vaccination in combination with micafungin resulted in 70% survival, while vaccine alone resulted in 40% and micafungin-treated arm had 20% significant survival when compared to 0% survival in the placebo arm (FIG. 11).

Additionally, we obtained sera from NDV-3A vaccinated female patients and tested the effect of the sera on binding to *C. auris*. The presence of cross-reactive antibodies was assessed in NDV-3A vaccinated women and in placebo women (that did not receive the NDV-3A vaccine) by ELISA against *C. auris* lysate supernatant. Cross-reactive antibodies were detected in NDV-3A vaccinated but not in the placebo group (FIG. 12A).

Biofilm formation by *C. auris* was also evaluated in the presence of 5% sera from NDV-3A vaccinated or placebo women. Percent reduction in biofilm formation was calculated for both vaccinated and placebo sera by dividing their respective pre-immunization serum OD values. As shown in FIG. 12B, serum from NDV-3A vaccinated women significantly reduces *C. auris* biofilm formation.

OTHER EMBODIMENTS

All publications, patents, and patent applications mentioned in the above specification are hereby incorporated by reference to the same extent as if each individual publication, patent or patent application was specifically and individually indicated to be incorporated by reference in its entirety.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of treating a subject for, immunizing a subject against, preventing in a subject, or inducing production of antibodies in a subject against, a *Candida auris* infection by administering to the subject an immunogenic amount of a *C. auris* Als3 polypeptide comprising at least one of SEQ ID NOs: 1-7, or an anti-*C. auris* Als3 antibody.

2. The method of claim 1, wherein the method inhibits or reduces *C. auris* biofilm formation in the subject relative to *C. auris* biofilm formation in an untreated.

3. The method of claim 1, wherein the subject has, is suspected of having, or is at risk of having a *C. auris* infection.

4. The method of claim 1, wherein the subject is immunocompromised.

5. The method of claim 1, wherein the subject suffers from a comorbidity or has a risk factor for *C. auris* infection.

6. The method of claim 5, wherein the risk factor is a surgery, stay in an intensive care unit, habitation in a nursing home, a breathing tube, a feeding tube, treatment with a broad-spectrum antibiotic or antifungal agent, or a catheter, such as a central venous catheter.

7. The method of claim 1, wherein the *C. auris* is multi-drug resistant.

8. The method of claim 1, wherein the method further comprises administration of an antifungal drug selected from the group consisting of an azole, a polyene, an allylamine, an echinocandin, a lanosterol demethylase inhibitor, benzoic acid, ciclopirox oamine, enfumafungin, 5-flucytosin, griseofulvin, haloprogin, tolnaftate, aminocandin, chlordantoin, chlorphenesin, nifuroxime, undecylenic acid, and crystal violet.

9. The method of claim 8, wherein:
a) the azole is a triazole, an imidazole, or a thiazole;
b) the polyene is amphotericin B, candicidin, filipin, hamycin, natamycin, nystatin, or rimocidin;
c) the allylamine is amorolfin, butenafine, naftifine, or terbinafine;
d) the echinocandin is anidulafungin, biafungin, caspofungin, or micafungin; or
e) the lanosterol demethylase inhibitor is VT-1161.

10. The method of claim 9, wherein:
a) the triazole is fluconazole, albaconazole, efinaconazole, epoxiconazole, isavuconazole, itraconazole, posaconazole, propiconazole, ravuconazole, terconazole, or voriconazole;
b) the imidazole is bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, or tioconazole; or
c) the thiazole is abafungin.

11. The method of claim 1, wherein the Als3 polypeptide is formulated with an adjuvant.

12. The method of claim 11, wherein the adjuvant is Freund's adjuvant, lipopolysaccharide, aluminum phosphate, aluminum hydroxide, or alum.

13. The method of claim 2, wherein the method inhibits or reduces *C. auris* biofilm formation by about 10%, 20%, 30%, 40%, 50%, 60%, 70%, 80%, 85%, or 90%.

14. The method of claim 2, wherein the method substantially eliminates *C. auris* biofilm formation.

* * * * *

SEQUENCE LISTING

```
<160> NUMBER OF SEQ ID NOS: 7

<210> SEQ ID NO 1
<211> LENGTH: 1119
<212> TYPE: PRT
<213> ORGANISM: Candida albicans

<400> SEQUENCE: 1

Met Leu Gln Gln Tyr Thr Leu Leu Leu Ile Tyr Leu Ser Val Ala Thr
1               5                   10                  15

Ala Lys Thr Ile Thr Gly Val Phe Asn Ser Phe Asn Ser Leu Thr Trp
            20                  25                  30

Ser Asn Ala Ala Thr Tyr Asn Tyr Lys Gly Pro Gly Thr Pro Thr Trp
        35                  40                  45

Asn Ala Val Leu Gly Trp Ser Leu Asp Gly Thr Ser Ala Ser Pro Gly
    50                  55                  60

Asp Thr Phe Thr Leu Asn Met Pro Cys Val Phe Lys Phe Thr Thr Ser
65                  70                  75                  80

Gln Thr Ser Val Asp Leu Thr Ala His Gly Val Lys Tyr Ala Thr Cys
                85                  90                  95

Gln Phe Gln Ala Gly Glu Glu Phe Met Thr Phe Ser Thr Leu Thr Cys
            100                 105                 110

Thr Val Ser Asn Thr Leu Thr Pro Ser Ile Lys Ala Leu Gly Thr Val
        115                 120                 125

Thr Leu Pro Leu Ala Phe Asn Val Gly Gly Thr Gly Ser Ser Val Asp
    130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                165                 170                 175

Asn Val Asp Pro Lys Gly Tyr Leu Thr Asp Ser Arg Val Ile Pro Ser
            180                 185                 190

Leu Asn Lys Val Ser Thr Leu Phe Val Ala Pro Gln Cys Ala Asn Gly
        195                 200                 205
```

-continued

```
Tyr Thr Ser Gly Thr Met Gly Phe Ala Asn Thr Tyr Gly Asp Val Gln
    210                 215                 220
Ile Asp Cys Ser Asn Ile His Val Gly Ile Thr Lys Gly Leu Asn Asp
225                 230                 235                 240
Trp Asn Tyr Pro Val Ser Ser Glu Ser Phe Ser Tyr Thr Lys Thr Cys
                245                 250                 255
Ser Ser Asn Gly Ile Phe Ile Thr Tyr Lys Asn Val Pro Ala Gly Tyr
            260                 265                 270
Arg Pro Phe Val Asp Ala Tyr Ile Ser Ala Thr Asp Val Asn Ser Tyr
        275                 280                 285
Thr Leu Ser Tyr Ala Asn Glu Tyr Thr Cys Ala Gly Tyr Trp Gln
    290                 295                 300
Arg Ala Pro Phe Thr Leu Arg Trp Thr Gly Tyr Arg Asn Ser Asp Ala
305                 310                 315                 320
Gly Ser Asn Gly Ile Val Ile Ala Thr Thr Arg Thr Val Thr Asp
                325                 330                 335
Ser Thr Thr Ala Val Thr Thr Leu Pro Phe Asp Pro Asn Arg Asp Lys
            340                 345                 350
Thr Lys Thr Ile Glu Ile Leu Lys Pro Ile Pro Thr Thr Thr Ile Thr
        355                 360                 365
Thr Ser Tyr Val Gly Val Thr Thr Ser Tyr Ser Thr Lys Thr Ala Pro
    370                 375                 380
Ile Gly Glu Thr Ala Thr Val Ile Val Asp Ile Pro Tyr His Thr Thr
385                 390                 395                 400
Thr Thr Val Thr Ser Lys Trp Thr Gly Thr Ile Thr Ser Thr Thr Thr
                405                 410                 415
His Thr Asn Pro Thr Asp Ser Ile Asp Thr Val Ile Val Gln Val Pro
            420                 425                 430
Ser Pro Asn Pro Thr Val Thr Thr Glu Tyr Trp Ser Gln Ser Phe
        435                 440                 445
Ala Thr Thr Thr Thr Ile Thr Gly Pro Pro Gly Asn Thr Asp Thr Val
    450                 455                 460
Leu Ile Arg Glu Pro Pro Asn His Thr Val Thr Thr Thr Glu Tyr Trp
465                 470                 475                 480
Ser Glu Ser Tyr Thr Thr Thr Ser Thr Phe Thr Ala Pro Pro Gly Gly
                485                 490                 495
Thr Asp Ser Val Ile Ile Lys Glu Pro Pro Asn Pro Thr Val Thr Thr
            500                 505                 510
Thr Glu Tyr Trp Ser Glu Ser Tyr Thr Thr Thr Ser Thr Phe Thr Ala
        515                 520                 525
Pro Pro Gly Gly Thr Asp Ser Val Ile Ile Lys Glu Pro Pro Asn His
    530                 535                 540
Thr Val Thr Thr Thr Glu Tyr Trp Ser Gln Ser Tyr Thr Thr Thr Thr
545                 550                 555                 560
Thr Val Thr Ala Pro Pro Gly Gly Thr Asp Val Leu Val Arg Glu
                565                 570                 575
Pro Pro Asn His Thr Val Thr Thr Thr Glu Tyr Trp Ser Gln Ser Tyr
            580                 585                 590
Thr Thr Thr Thr Thr Val Ile Ala Pro Pro Gly Gly Thr Asp Ser Val
        595                 600                 605
Ile Ile Arg Glu Pro Pro Asn Pro Thr Val Thr Thr Thr Glu Tyr Trp
    610                 615                 620
```

```
Ser Gln Ser Tyr Ala Thr Thr Thr Ile Thr Ala Pro Pro Gly Glu
625                 630             635             640

Thr Asp Thr Val Leu Ile Arg Glu Pro Pro Asn His Thr Val Thr Thr
                645             650             655

Thr Glu Tyr Trp Ser Gln Ser Tyr Ala Thr Thr Thr Ile Thr Ala
            660             665             670

Pro Pro Gly Glu Thr Asp Thr Val Leu Ile Arg Glu Pro Pro Asn His
            675             680             685

Thr Val Thr Thr Thr Glu Tyr Trp Ser Gln Ser Phe Ala Thr Thr Thr
    690             695             700

Thr Val Thr Ala Pro Pro Gly Gly Thr Asp Thr Val Ile Ile Arg Glu
705             710             715             720

Pro Pro Asn His Thr Val Thr Thr Thr Glu Tyr Trp Ser Gln Ser Tyr
                725             730             735

Ala Thr Thr Thr Thr Ile Thr Ala Pro Pro Gly Glu Thr Asp Thr Val
                740             745             750

Leu Ile Arg Glu Pro Pro Asn His Thr Val Thr Thr Thr Glu Tyr Trp
            755             760             765

Ser Gln Ser Tyr Ala Thr Thr Thr Thr Ile Ile Ala Pro Pro Gly Glu
770             775             780

Thr Asp Thr Val Leu Ile Arg Glu Pro Pro Asn Pro Thr Val Thr Thr
785             790             795             800

Thr Glu Tyr Trp Ser Gln Ser Tyr Thr Thr Ala Thr Val Thr Ala
            805             810             815

Pro Pro Gly Gly Thr Asp Thr Val Ile Ile Tyr Asp Thr Met Ser Ser
            820             825             830

Ser Glu Ile Ser Ser Phe Ser Arg Pro His Tyr Thr Asn His Thr Thr
            835             840             845

Leu Trp Ser Thr Thr Trp Val Ile Glu Thr Lys Thr Ile Thr Glu Thr
850             855             860

Ser Cys Glu Gly Asp Lys Gly Cys Ser Trp Val Ser Val Ser Thr Arg
865             870             875             880

Ile Val Thr Ile Pro Asn Asn Ile Glu Thr Pro Met Val Thr Asn Thr
                885             890             895

Val Asp Ser Thr Thr Thr Glu Ser Thr Ser Gln Ser Pro Ser Gly Ile
                900             905             910

Phe Ser Glu Ser Gly Val Ser Val Glu Thr Glu Ser Ser Thr Val Thr
            915             920             925

Thr Ala Gln Thr Asn Pro Ser Val Pro Thr Thr Glu Ser Glu Val Val
930             935             940

Phe Thr Thr Lys Gly Asn Asn Glu Asn Gly Pro Tyr Glu Ser Pro Ser
945             950             955             960

Thr Asn Val Lys Ser Ser Met Asp Glu Asn Ser Glu Phe Thr Thr Ser
                965             970             975

Thr Ala Ala Ser Thr Ser Thr Asp Ile Glu Asn Glu Thr Ile Ala Thr
            980             985             990

Thr Gly Ser Val Glu Ala Ser Ser Pro Ile Ile Ser Ser Ser Ala Asp
            995             1000            1005

Glu Thr Thr Thr Val Thr Thr Thr Ala Glu Ser Thr Ser Val Ile
    1010            1015            1020

Glu Gln Pro Thr Asn Asn Asn Gly Gly Gly Lys Ala Pro Ser Ala
    1025            1030            1035
```

```
Thr Ser  Ser Pro Ser Thr  Thr Thr Ala Asn Asn  Asp Ser Val
    1040         1045              1050

Ile Thr  Gly Thr Thr Ser  Thr Asn Gln Ser Gln  Ser Gln Ser Gln
    1055         1060              1065

Tyr Asn  Ser Asp Thr Gln Gln  Thr Thr Leu Ser Gln  Gln Met Thr
    1070             1075                  1080

Ser Ser  Leu Val Ser Leu His  Met Leu Thr Thr Phe  Asp Gly Ser
    1085             1090                  1095

Gly Ser  Val Ile Gln His Ser  Thr Trp Leu Cys Gly  Leu Ile Thr
    1100             1105                  1110

Leu Leu  Ser Leu Phe Ile
    1115

<210> SEQ ID NO 2
<211> LENGTH: 416
<212> TYPE: PRT
<213> ORGANISM: Candida albicans

<400> SEQUENCE: 2

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270
```

```
Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
        290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Ile Thr Thr
                340                 345                 350

Ser Tyr Val Gly Val Thr Thr Ser Tyr Leu Thr Lys Thr Ala Pro Ile
        355                 360                 365

Gly Glu Thr Ala Thr Val Ile Val Asp Ile Pro Tyr His Thr Thr Thr
        370                 375                 380

Thr Val Thr Ser Lys Trp Thr Gly Thr Ile Thr Ser Thr Thr Thr His
385                 390                 395                 400

Thr Asn Pro Thr Asp Ser Ile Asp Thr Val Ile Val Gln Val Pro Leu
                405                 410                 415
```

<210> SEQ ID NO 3
<211> LENGTH: 425
<212> TYPE: PRT
<213> ORGANISM: Candida albicans

<400> SEQUENCE: 3

```
His His His His His His Gly Ile Gln Lys Thr Ile Thr Gly Val Phe
1               5                   10                  15

Asn Ser Phe Asn Ser Leu Thr Trp Ser Asn Ala Ala Thr Tyr Asn Tyr
            20                  25                  30

Lys Gly Pro Gly Thr Pro Thr Trp Asn Ala Val Leu Gly Trp Ser Leu
        35                  40                  45

Asp Gly Thr Ser Ala Ser Pro Gly Asp Thr Phe Thr Leu Asn Met Pro
    50                  55                  60

Cys Val Phe Lys Phe Thr Thr Ser Gln Thr Ser Val Asp Leu Thr Ala
65                  70                  75                  80

His Gly Val Lys Tyr Ala Thr Cys Gln Phe Gln Ala Gly Glu Glu Phe
                85                  90                  95

Met Thr Phe Ser Thr Leu Thr Cys Thr Val Ser Asn Thr Leu Thr Pro
            100                 105                 110

Ser Ile Lys Ala Leu Gly Thr Val Thr Leu Pro Leu Ala Phe Asn Val
        115                 120                 125

Gly Gly Thr Gly Ser Ser Val Asp Leu Glu Asp Ser Lys Cys Phe Thr
    130                 135                 140

Ala Gly Thr Asn Thr Val Thr Phe Asn Asp Gly Gly Lys Lys Ile Ser
145                 150                 155                 160

Ile Asn Val Asp Phe Glu Arg Ser Asn Val Asp Pro Lys Gly Tyr Leu
                165                 170                 175

Thr Asp Ser Arg Val Ile Pro Ser Leu Asn Lys Val Ser Thr Leu Phe
            180                 185                 190

Val Ala Pro Gln Cys Ala Asn Gly Tyr Thr Ser Gly Thr Met Gly Phe
        195                 200                 205

Ala Asn Thr Tyr Gly Asp Val Gln Ile Asp Cys Ser Asn Ile His Val
    210                 215                 220
```

```
Gly Ile Thr Lys Gly Leu Asn Asp Trp Asn Tyr Pro Val Ser Ser Glu
225                 230                 235                 240

Ser Phe Ser Tyr Thr Lys Thr Cys Ser Ser Asn Gly Ile Phe Ile Thr
                245                 250                 255

Tyr Lys Asn Val Pro Ala Gly Tyr Arg Pro Phe Val Asp Ala Tyr Ile
            260                 265                 270

Ser Ala Thr Asp Val Asn Ser Tyr Thr Leu Ser Tyr Ala Asn Glu Tyr
            275                 280                 285

Thr Cys Ala Gly Gly Tyr Trp Gln Arg Ala Pro Phe Thr Leu Arg Trp
            290                 295                 300

Thr Gly Tyr Arg Asn Ser Asp Ala Gly Ser Asn Gly Ile Val Ile Val
305                 310                 315                 320

Ala Thr Thr Arg Thr Val Thr Asp Ser Thr Ala Val Thr Leu
                325                 330                 335

Pro Phe Asp Pro Asn Arg Asp Lys Thr Lys Thr Ile Glu Ile Leu Lys
                340                 345                 350

Pro Ile Pro Thr Thr Thr Ile Thr Thr Ser Tyr Val Gly Val Thr Thr
                355                 360                 365

Ser Tyr Leu Thr Lys Thr Ala Pro Ile Gly Glu Thr Ala Thr Val Ile
            370                 375                 380

Val Asp Ile Pro Tyr His Thr Thr Thr Val Thr Ser Lys Trp Thr
385                 390                 395                 400

Gly Thr Ile Thr Ser Thr Thr His Thr Asn Pro Thr Asp Ser Ile
                405                 410                 415

Asp Thr Val Ile Val Gln Val Pro Leu
            420                 425

<210> SEQ ID NO 4
<211> LENGTH: 307
<212> TYPE: PRT
<213> ORGANISM: Candida albicans

<400> SEQUENCE: 4

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
                20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
        50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Phe Asn
        130                 135                 140

Asp Gly Gly Lys Lys Ile Ser Ile Asn Val Asp Phe Glu Arg Ser Asn
145                 150                 155                 160
```

```
Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly
305

<210> SEQ ID NO 5
<211> LENGTH: 108
<212> TYPE: PRT
<213> ORGANISM: Candida albicans

<400> SEQUENCE: 5

Ile Val Ile Val Ala Thr Thr Arg Thr Val Thr Asp Ser Thr Thr Ala
1               5                   10                  15

Val Thr Thr Leu Pro Phe Asp Pro Asn Arg Asp Lys Thr Lys Thr Ile
            20                  25                  30

Glu Ile Leu Lys Pro Ile Pro Thr Thr Ile Thr Thr Ser Tyr Val
        35                  40                  45

Gly Val Thr Thr Ser Tyr Ser Thr Lys Thr Ala Pro Ile Gly Glu Thr
    50                  55                  60

Ala Thr Val Ile Val Asp Ile Pro Tyr His Thr Thr Thr Val Thr
65                  70                  75                  80

Ser Lys Trp Thr Gly Thr Ile Thr Ser Thr Thr His Thr Asn Pro
                85                  90                  95

Thr Asp Ser Ile Asp Thr Val Ile Val Gln Val Pro
            100                 105

<210> SEQ ID NO 6
<211> LENGTH: 861
<212> TYPE: PRT
<213> ORGANISM: Candida auris

<400> SEQUENCE: 6

Met Lys Ile Ile Ser Leu Leu Trp Cys Leu Ala Leu Leu Tyr Gly Asn
1               5                   10                  15

Ala Leu Ala Ala Pro Gln Thr Gly Val Phe Thr Ser Ile Asp Ser Leu
            20                  25                  30

Thr Pro Phe Asp Val Ala Trp Pro Met Met Pro Gly Trp Asp Ala Thr
        35                  40                  45

Val Ser Trp His Ile Asn Ser Ser Met Glu Met Lys Asp Gly Asp Thr
    50                  55                  60
```

```
Phe Phe Leu Arg Ile Pro Phe Val Ile Glu Phe Asn Thr Asp Glu Ser
 65                  70                  75                  80

Ser Ile Gln Met Ser Asp Gly Thr Asn Thr Phe Ala Asn Cys Val Leu
             85                  90                  95

Thr Pro Gly Glu Asn Leu Val Pro Tyr Ser Glu Val Lys Cys Thr Ala
            100                 105                 110

Thr Thr Gln Val Glu Asp Val Gln Ser Ser Ser Gly Thr Ile Thr Phe
            115                 120                 125

Pro Ile Val Phe Asn Ala Gly Phe Ser Ala Gln Glu Leu Asp Leu Lys
            130                 135                 140

Ala Ala Asn His Trp Arg Thr Gly Ser Asn Thr Leu Glu Trp Thr Asp
145                 150                 155                 160

Gly Ser Asn Thr Leu Thr His Pro Ile Thr Phe Val Gly Gly Thr Met
                165                 170                 175

Ser Ala Phe Asn Gly Arg Pro Lys Arg Gly Ile Leu Asp Gln Arg Ser
                180                 185                 190

Phe Val Ser Thr Asn Thr Ile Arg Gln Phe Leu Met Gly Pro Leu Cys
            195                 200                 205

His Ser Ser Asp Met Ser Gly Glu Leu Ser Ile Glu Asn Leu Leu Glu
            210                 215                 220

Glu Ala Pro Phe Asp Cys Asp Ser Ile Thr Thr Ala Met Ser Asn Gln
225                 230                 235                 240

Ile Asn Ala Trp Tyr Phe Pro Gln Thr Ala Asp Glu Ala Glu Ala Thr
                245                 250                 255

Ile Val Ser Cys Ser Ala Ala Gly Val Asn Val Ala Phe Ser Asn Leu
                260                 265                 270

Pro Ala Gly Phe Arg Pro Tyr Ile Asn Ile Asp Ala Thr Lys Lys Ile
                275                 280                 285

Ala Val Ser Glu Ile Asp Asn Ile Tyr His Tyr Asn Phe Thr Cys Asn
            290                 295                 300

Gly Ala Glu Leu Ser Asp Ser Ile Phe Ala Ala Trp Asp Gln Phe Phe
305                 310                 315                 320

Ser Asp Asp Thr Glu Glu Asp Thr Leu Thr Gln Val Val Thr
            325                 330                 335

Thr Ala Thr Asp Pro Gly Ile Thr Ala Thr Ser Ile Ala Thr His Thr
            340                 345                 350

Gly Thr Asp Ala Asn Thr Ile Val Asn Val Pro Ile Ser Glu Ser
            355                 360                 365

Thr Val Ile Val Thr Gly Thr Asn Ser Ile Ala Thr Thr Lys Thr Phe
            370                 375                 380

Thr Ser Ser Gly Thr Arg Ile Val Ser Ile Asp Thr Pro Ile Pro Thr
385                 390                 395                 400

Ser Thr Ile Thr Ser Thr Trp Thr Glu Ser Val Thr Ser Thr Tyr Thr
                405                 410                 415

Val Pro Ala Ser Pro Gly Val Thr Ala Ser Val Ile Val Glu Val Pro
            420                 425                 430

Ile Pro Thr Thr Thr Ile Thr Gln Thr Trp Thr Gly Met Glu Thr Met
            435                 440                 445

Thr Gln Thr Leu Pro Ala Glu Ile Gly Glu Thr Gln Ser Val Ile Val
            450                 455                 460

Asn Ile Pro Asp Ser Thr Thr Ile Met Ser Ser Asn Glu Ala Thr Ser
465                 470                 475                 480
```

```
Glu Gln Thr Met Ser Leu Ser Val Asp Thr Ile Pro Thr Ser Leu Met
                485                 490                 495
Asn Ser Ser Thr Ser Ser Gly Ala Ser Leu Ser Glu Glu Ile Ser Thr
            500                 505                 510
Gln Glu Thr Ser Leu Ser Ser Gln Ser Ser Asp Glu Ser Val Ser Gln
        515                 520                 525
Thr Glu Ser Tyr Thr Ala Ser Asp Pro Ser Pro Val Ser Ser Ser
    530                 535                 540
Phe Leu Asn Thr Ser Ser Lys Ile Gly Ser Gln Leu Leu Leu Ser
545                 550                 555                 560
Ser Gln Ser Asp Pro Val Ser Thr Ser Glu Met Ala Pro Gln Ser Gly
                565                 570                 575
Ile Ser Ser Tyr Ile Thr Ser Trp Ile Gly Ser Ile Thr Val Pro Ser
            580                 585                 590
Ser Leu Ser Ala Glu Thr Asp Ser Ala Gln Glu Thr Ser Tyr His Thr
        595                 600                 605
Thr Lys Ser Pro Thr Asp Asn Ser Ala Ser Glu Asn Val Tyr Leu Thr
    610                 615                 620
Glu Ser Lys Lys Thr Glu Asn Thr Asp Thr Lys Ala Ser His Ser Val
625                 630                 635                 640
Ile Ser Thr Ser Gly Thr Ser Asp Ile Asn Asp Ser Ser Ser Asp Ala
                645                 650                 655
Tyr Ile Asp Pro Ser Ile Ser Thr Thr Ile Gly Val Pro Ser Ile
            660                 665                 670
Ser Val Asn Trp Asn Ser Ser Phe Val Ile Thr Thr Leu Val Ser Glu
        675                 680                 685
Thr Thr Cys Ile Ser Ser Thr Pro Lys Thr Val Ser Glu Thr Leu Asp
    690                 695                 700
Ile Gln Asp Leu Phe Ser Thr Cys Lys Glu Ala Ser Ala Lys Thr Asn
705                 710                 715                 720
Asn Glu Gly Ser Leu Lys Ala Ser Lys Leu Ser Lys Ser Thr Ser Lys
                725                 730                 735
Ile Asp Thr Lys Val Ile Phe Pro Thr Ser Glu Pro Asp Phe Ile Ala
            740                 745                 750
Ser Thr Ser Ser Tyr Trp Ser Gln Asp Ile Gln Ser Ser Asn Gln Phe
        755                 760                 765
Asn Ile Met Thr Ser Pro Asp Ile Ser Leu Ala Gln Ser Gly Pro Thr
    770                 775                 780
Glu Leu Ala Leu Ala Arg Cys Thr Ser Ala Asn Cys Gly Thr Gln Thr
785                 790                 795                 800
Asn Ser Lys Gly Gln Asn Pro Asn Val Ala Thr Ser Leu Met Ser Ile
                805                 810                 815
Ser Asn Ser Asp Ala Pro Ala Val Ser Pro Ser Ser Gln Leu Pro
            820                 825                 830
Ser Val Leu Thr Tyr Ser Gly Ile Ser Ser Thr Leu Lys Val Ser Gly
        835                 840                 845
Ile Leu Ala Met Phe Val Ser Leu Thr Gln Ile Leu Phe
    850                 855                 860

<210> SEQ ID NO 7
<211> LENGTH: 714
<212> TYPE: PRT
<213> ORGANISM: Candida auris
```

<400> SEQUENCE: 7

```
Met Leu Ala Tyr Thr Ile Ala Ser Pro Ala Ile Lys Pro Glu Ser
1               5                   10                  15

Asp Val Glu Lys Ser Glu Val Lys Asn Thr Glu Asp Glu Asn Thr Ser
            20                  25                  30

Glu Ala Gln Asp Asp Ser Ala Asn Pro Glu Val Gln Leu Pro Glu Pro
        35                  40                  45

Leu Thr Met Glu Thr Phe Asp Asp Phe Thr Ser Gln His Ile Thr Phe
    50                  55                  60

Val Glu Phe Phe Ser Pro Tyr Cys His His Cys Gln Ala Leu Ala Pro
65              70                  75                  80

Lys Trp Glu Gln Ala Phe Arg Glu Thr Tyr Glu Gln Gln Lys Thr
                85                  90                  95

Gly Leu His Met Arg Gln Val Asn Cys Val Glu Ser Gly Asp Leu Cys
                100                 105                 110

Asp Arg Glu Val Val Pro Tyr Trp Pro Asn Met Arg Val Tyr Val Pro
            115                 120                 125

Glu Arg Asp Glu Lys Gly Glu Lys Thr Gly Lys Gly Lys Leu Val Asp
        130                 135                 140

Ser Phe Pro Arg Ala Leu Lys Gln Thr Pro Lys Asn Leu Lys Lys Phe
145                 150                 155                 160

Met Met Asn Ser Leu Ala Glu Tyr Ala Asp Gly Thr Ile Ser Met Pro
                165                 170                 175

Ser Ser Ser Glu Leu Leu Asn Thr Asp Ser Met Leu Asn Ile Val Ala
                180                 185                 190

Gly Glu Met Asn Glu Pro Trp Phe Val Gly Met Phe Ser Ser Ser Asn
                195                 200                 205

Glu Glu Trp Glu Lys Gly Thr Phe Ser Arg Ser Cys Met Asp Cys Leu
        210                 215                 220

Arg Ile Lys Ser Asp Trp Asp Arg Leu Ser Asn Leu Ile Gln Ser Ser
225                 230                 235                 240

Thr Lys Ser Gly His Leu Asn Cys Lys Ser Asn Pro Thr Leu Cys Glu
                245                 250                 255

Lys Leu Gly Tyr Pro Glu Leu Ser Ser Asp Met Arg Gln Ala Pro Lys
                260                 265                 270

Phe Ala Met Phe Leu Pro Ser Lys Val Gly Arg Ile Arg Phe Asp Tyr
            275                 280                 285

Asn Asp Ile Val Asp Val Lys Lys Met Lys Ala Trp Ile Ser Arg Leu
290                 295                 300

Ala Ile Asn Ser Gln Tyr Glu Met Ala Thr Ala Gly His Leu Glu Asp
305                 310                 315                 320

Leu Asp Leu Phe Val Thr Glu Lys Pro Ser Ser Pro Leu Gln Val Glu
                325                 330                 335

Leu Pro Leu Asn Thr Lys Val Gly Leu Val Phe Ala Phe Glu Lys Asn
            340                 345                 350

Lys Leu Thr Lys Glu Asp Lys Ala Ile Leu Pro His Leu Leu Glu Met
            355                 360                 365

Ile Thr Asp Leu Pro Phe Asn Val Arg Leu Tyr Ala Ser His Ser Val
        370                 375                 380

Lys Phe Glu Glu Thr Leu Glu Tyr Gln Ser Lys Gly Leu Ile Asp Phe
385                 390                 395                 400
```

-continued

```
Val Lys Thr Asp Pro Thr Leu Glu Glu Val Thr Tyr Ser Arg Pro Leu
            405                 410                 415

His Ile Ala Thr Thr Leu Thr Lys Lys Pro Thr Leu Tyr Leu Phe Lys
            420                 425                 430

Glu Asn Ser Met Ile Pro Thr Val Tyr Gln Asn Tyr Ala Pro Glu Asp
            435                 440                 445

Met Arg Asp Pro Glu Lys Ile Lys Ala Trp Val Met Lys Asn Ile Tyr
            450                 455                 460

Pro Leu Phe Asp Glu Leu Thr Pro Glu Leu Leu Lys Trp Tyr Phe Asn
465                 470                 475                 480

Thr Lys Asp Lys Arg Asn Asp Lys Val Val Val Thr Phe Val Asp Gly
            485                 490                 495

Asn Asp Asp Lys His Leu Lys Glu Ala Leu Tyr Asn Val Ser Leu Val
            500                 505                 510

Ala His Glu Tyr Thr Leu Leu Lys Lys Gln Tyr Tyr Phe Lys Ala Leu
            515                 520                 525

Gln Asp Glu Arg Ser Ser Lys Trp Gln Lys Ile Thr Glu Leu Arg Glu
530                 535                 540

Lys Gly Ala Lys Ser Ser Glu Val Ile Lys Ala Met Lys Glu Tyr Val
545                 550                 555                 560

Pro His Leu Phe Asp His Asn Asp Ala Leu Phe Thr Tyr Val Asn Leu
            565                 570                 575

Arg Glu Tyr Pro Arg Phe Ala Lys Asp Ile Gly Trp Asp Ile Asp Gly
            580                 585                 590

Glu Gly Tyr Lys Pro Gly Asp Thr Ile Ile Val Asn Lys Asn Thr Lys
            595                 600                 605

Tyr Tyr Tyr Asp Arg Thr Leu Thr Gly Glu Lys Leu Thr Ile Glu Pro
610                 615                 620

Ser Lys Leu Arg Pro Val Leu Leu His Leu Leu Asp Pro Gln Leu Thr
625                 630                 635                 640

Lys Asp Ala Lys Val Val Gly Phe Ser Pro Arg Leu Ala Ala Ser Pro
            645                 650                 655

Phe Thr Gly Tyr Leu Arg Phe Met Asp Gln Ile Tyr Gln His Gly Ile
            660                 665                 670

Val Gly Ile Ile Leu Phe Phe Ile Gly Val Phe Leu Phe Leu Lys Met
            675                 680                 685

Ala Leu Arg Phe Met Lys Arg Gly Lys His Thr Ser Arg Ser Arg Gly
            690                 695                 700

Ile Ile Gly Asn Val Ala Pro Lys His Asp
705                 710
```